US007422880B2

(12) United States Patent
Rybak et al.

(10) Patent No.: US 7,422,880 B2
(45) Date of Patent: Sep. 9, 2008

(54) METHOD FOR PRODUCING AN L-AMINO ACID USING A BACTERIUM OF THE ENTEROBACTERIACEAE FAMILY HAVING A PATHWAY OF GLYCOGEN BIOSYNTHESIS DISRUPTED

(75) Inventors: Konstantin Vyacheslavovich Rybak, Moscow (RU); Ekaterina Aleksandrovna Slivinskaya, Moscow (RU); Elvira Borisovna Voroshilova, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 227 days.

(21) Appl. No.: 11/275,569

(22) Filed: Jan. 17, 2006

(65) Prior Publication Data
US 2006/0160192 A1  Jul. 20, 2006

Related U.S. Application Data

(60) Provisional application No. 60/703,426, filed on Jul. 29, 2005.

(30) Foreign Application Priority Data
Jan. 19, 2005   (RU) ............................. 2005101110

(51) Int. Cl.
*C12N 9/00* (2006.01)
*C12N 1/20* (2006.01)
(52) U.S. Cl. .................................... 435/183; 435/252.3
(58) Field of Classification Search ................ 435/183, 435/252.3
See application file for complete search history.

(56) References Cited

U.S. PATENT DOCUMENTS

| 6,960,455 | B2 | 11/2005 | Livshits et al. |
| 2004/0038380 | A1 | 2/2004 | Debabov et al. |
| 2004/0132165 | A1 | 7/2004 | Akhverdian et al. |
| 2004/0229320 | A1 | 11/2004 | Stoynova et al. |
| 2004/0229321 | A1 | 11/2004 | Savrasova et al. |
| 2005/0048631 | A1 | 3/2005 | Klyachko et al. |
| 2005/0054061 | A1 | 3/2005 | Klyachko et al. |
| 2005/0124048 | A1 | 6/2005 | Akhverdian et al. |
| 2005/0176033 | A1 | 8/2005 | Klyachko et al. |
| 2005/0214911 | A1 | 9/2005 | Marchenko et al. |
| 2005/0214913 | A1 | 9/2005 | Marchenko et al. |
| 2005/0239175 | A1 | 10/2005 | Tabolina et al. |
| 2006/0030009 | A1 | 2/2006 | Livshits et al. |
| 2006/0035346 | A1 | 2/2006 | Savrasova et al. |
| 2006/0040365 | A1 | 2/2006 | Kozlov et al. |

OTHER PUBLICATIONS

International Preliminary Report on Patentability for PCT Patent App. No. PCT/JP2006/301089 (Aug. 2, 2007).
Suzuki, K., et al., "Regulatory Circuitry of the CsrA/CsrB and BarA/UvrY Systems of *Escherichia coli*," J. Bacteriol. 2002;184(18):5130-5140.
Tatarko, M., et al., "Disruption of a Global Regulatory Gene to Enhance Central Carbon Flux into Phenylalanine Biosynthesis in *Escherichia coli*," Curr. Microbiol. 2001;43:26-32.
White, D., et al., "Phylogenetic distribution of global regulatory gene *crsA* among eubacteria," Gene 1996;182:221-223.
International Search Report and Written Opinion of the International Searching Authority for PCT Patent App. No. PCT /JP2006/301089 (Sep. 28, 2006).
Baker, C. S., et al., "CsrA regulates glycogen biosynthesis by preventing translation of *glgC* in *Escherichia coli*," Mol. Microbiol. 2002;44(6):1599-1610.
Flatterick, R. J., et al., "The Structures and Related Functions of Phosphorylase α," Ann. Rev. Biochem. 1980;49:31-61.
Haugen, T. H., et al., "Biosynthesis of Bacterial Glycogen," J. Biol. Chem. 1976;251(24):7880-7885.
Hengge-Aronis, R., et al., "Identification and molecular analysis of *glgS*, a novel growth-phase-regulated and *rpoS*-dependant gene involved in glycogen synthesis *Escherichia coli*,"Mol. Microbiol. 1992;6(14):1877-1886.
Kozlov, G., et al., "Structure of GlgS from *Escherichia coli* suggests a role in protein-protein interaction," BMC Biol. 2004:2(10):1-7.
Preiss, J., "Bacterial Glycogen Synthesis and Its Regulation," Ann. Rev. Microbiol. 1984;38:419-458.
Romeo, T., et al., "Analysis of the *Escherichia coli* glycogen gene cluster suggests that catabolic enzymes are encoded among the biosynthetic genes," Gene 1988;70:363-376.
Romeo, T., et al., "Genetic Regulation of Glycogen Biosynthesis in *Escherichia coli*: In Vitro Effects of Cyclic AMP and Guanosine 5'-Diphosphate and Analysis of In Vivo Transcripts," 1989;171(5):2773-2782.
Preiss, J., et al., "Molecular Biology and Regulatory Aspect of Glycogen Biosynthesis in Bacteria," Prog. Nucleic Acid Res. Mol. Biol. 1994;47:299-329.

*Primary Examiner*—Tekchand Saidha
(74) *Attorney, Agent, or Firm*—Shelly Guest Cermak; Cermak Kenealy & Vaidya LLP

(57) ABSTRACT

There is provided a method for producing an L-amino acid using a bacterium of the *Enterobacteriaceae* family, particularly a bacterium belonging to the genus *Escherichia* or *Pantoea*, having the glycogen biosynthesis pathway disrupted.

10 Claims, 3 Drawing Sheets

US 7,422,880 B2

METHOD FOR PRODUCING AN L-AMINO ACID USING A BACTERIUM OF THE ENTEROBACTERIACEAE FAMILY HAVING A PATHWAY OF GLYCOGEN BIOSYNTHESIS DISRUPTED

This application claims priority under 35 U.S.C. §119(a) to Russian patent application 2005101110, filed Jan. 19, 2005, and under 35 U.S.C. §119(e) to U.S. provisional patent application 60/703,426, filed Jul. 29, 2005, the entireties of both are hereby incorporated by reference. The Sequence Listing on Compact Disk filed herewith is also hereby incorporated by reference in its entirety (File Name: US-199 Seq List; File Size: 73 KB; Date Created: Jan. 17, 2006).

BACKGROUND OF THE INVENTION

1. Field of Invention

The present invention relates to the microbiological industry, and specifically to a method for producing an L-amino acid using a bacterium of the *Enterobacteriaceae* family, wherein the glycogen biosynthesis pathway has been disrupted.

2. Description of the Related Art

Glycogen represents the major form of stored carbon for *Escherichia coli* and many other prokaryotes, and provides a readily metabolized substrate for maintenance energy. Glycogen accumulation in *Escherichia coli* is inversely related to the growth rate, and occurs most actively when cells enter the stationary phase. The levels of the three biosynthetic enzymes undergo corresponding changes under these conditions, suggesting that genetic control of enzyme biosynthesis may account for at least part of the regulation (Preiss, J., Annu. Rev. Microbiol. 38, 419-458 (1984)). In *Escherichia coli*, the structural genes for glycogen biosynthesis are clustered on adjacent operons—glgBX and glgCAP. Interestingly, the glycogen biosynthetic (glgCA) and degradative (glgP) genes are localized together in a cluster, possibly to facilitate the regulation of these systems in vivo (Romeo, T., Gene. 70(2), 363-76 (1988)). The glgC gene is the structural gene for glucose-1-phosphate adenylyltransferase. Synonyms for glucose-1-phosphate adenylyltransferase are ADP-glucose synthase, ADP-glucose pyrophosphorylase, ADP: α-D-glucose-1-phosphate adenylyltransferase, GlgC protein.

Glucose-1-phosphate adenylyltransferase (EC 2.7.7.27) is an allosteric enzyme in the glycogen biosynthetic pathway of eubacteria. Among the enteric bacteria, glucose-1-phosphate adenylyltransferase is regulated by glycolytic intermediates with fructose 1,6-biphosphate as the activator and AMP, ADP, and $P_i$ as inhibitors. The enzyme catalyzes the synthesis of ADP glucose and $PP_i$ from glucose 1-phosphate and ATP. This reaction is the first unique step in bacterial glycogen biosynthesis.

It is known that the carbon storage regulatory system of *Escherichia coli* controls the expression of genes involved in carbohydrate metabolism and cell motility. CsrA binding to glgCAP transcripts inhibits glycogen metabolism by promoting glgCAP mRNA decay. CsrB RNA functions as an antagonist of CsrA by sequestering this protein and preventing its action (Baker, C. S. et al, Mol. Microbiol., 44(6), 1599-610 (2002)).

The glgCAP operon is under the positive control of cyclic AMP (cAMP) and the cAMP receptor protein (CRP). Both the cya gene encoding adenylate cyclase (EC 4.6.1.1) and the crp gene encoding CRP are required for optimal synthesis of glycogen (Fletterick, R. J. and Madsen, N. B., Annu. Rev. Biochem., 49, 31-61 (1980)). CRP binds to a site located upstream of the glgC gene. Glycogen synthesis in *E. coli* is also positively regulated by ppGpp, which stimulates the transcription of the glgCAP operon (Preiss. J., and Romeo, T., Prog. Nucleic Acid Res. Mol. Biol. 47, 299-329 (1994)).

By using a mini-Mu random chromosomal library and screening for glycogen overproduction, a novel gene (glgS) involved in glycogen synthesis was identified (Hengge-Aronis, R. and Fischer, D., Mol Microbiol. 6, 14, 1877-86 (1992)). It was also shown that the *Escherichia coli* protein GlgS is up-regulated in response to starvation stress and its overexpression was shown to stimulate glycogen synthesis (Kozlov, G. et al, BMC Biol., 2, 1, 10 (2004)).

The initial substrate for glycolysis biosynthesis is glucose-1-P, obtained from glucose-6-P, so said pathway competes with glycolysis for glucose-6-P. But currently, there have been no reports of inactivating the glgBX and/or glgCAP operons or inactivating the glgS gene for producing L-amino acids.

SUMMARY OF THE INVENTION

Objects of the present invention include enhancing the productivity of L-amino acid producing strains and providing a method for producing an L-amino acid using these strains.

The above objects were achieved by finding that inactivating the glgBX and/or glgCAP operons can enhance production of L-amino acids, such as L-threonine, L-lysine, L-cysteine, L-leucine, L-histidine, L-glutamic acid, L-phenylalanine, L-tryptophan, L-proline, and L-arginine.

The present invention provides a bacterium of the *Enterobacteriaceae* family having an increased ability to produce amino acids, such as L-threonine, L-lysine, L-cysteine, L-leucine, L-histidine, L-glutamic acid, L-phenylalanine, L-tryptophan, L-proline, and L-arginine.

It is an object of the present invention to provide an L-amino acid-producing bacterium of the *Enterobacteriaceae* family, wherein the bacterium has been modified so that the glycogen biosynthesis pathway is disrupted.

It is a further object of the present invention to provide the bacterium as described above, wherein the glycogen biosynthesis pathway is disrupted by attenuation of expression of the glgBX and/or glgCAP operons.

It is a further object of the present invention to provide the bacterium as described above, wherein the glycogen biosynthesis pathway is disrupted by inactivation of the glgBX and/or glgCAP operons.

It is a further object of the present invention to provide the bacterium as described above, wherein the inactivation of the glgBX and/or glgCAP operons is performed by deletion of a gene selected from a group consisting of glgB, glgX, glgC, glgA, glgP, and combinations thereof.

It is a further object of the present invention to provide the bacterium as described above, wherein the glycogen biosynthesis pathway is disrupted by attenuation of expression of the glgS gene.

It is a further object of the present invention to provide the bacterium as described above, wherein the glycogen biosynthesis pathway is disrupted by inactivation of the glgS gene.

It is a further object of the present invention to provide the bacterium as described above, wherein the bacterium belongs to the genus *Escherichia*.

It is a further object of the present invention to provide the bacterium as described above, wherein the bacterium belongs to the genus *Pantoea*.

It is a further object of the present invention to provide the bacterium as described above, wherein said L-amino acid is selected from the group consisting of an aromatic L-amino acid and a non-aromatic L-amino acid.

It is a further object of the present invention to provide the bacterium as described above, wherein said aromatic L-amino acid is selected from the group consisting of L-phenylalanine, L-tyrosine, and L-tryptophan.

It is a further object of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

It is a further object of the present invention to provide a method for producing an L-amino acid comprising:

cultivating the bacterium as described above in a medium to produce and excrete L-amino acid into the medium, and collecting said L-amino acid from the medium.

It is a further object of the present invention to provide the method as described above, wherein said L-amino acid is selected from the group consisting of an aromatic L-amino acid and a non-aromatic L-amino acid.

It is a further object of the present invention to provide the method as described above, wherein said aromatic L-amino acid is selected from the group consisting of L-phenylalanine, L-tyrosine, and L-tryptophan.

It is a further object of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

DETAILED DESCRIPTION OF THE PREFERRED EMBODIMENTS

Figure 1:
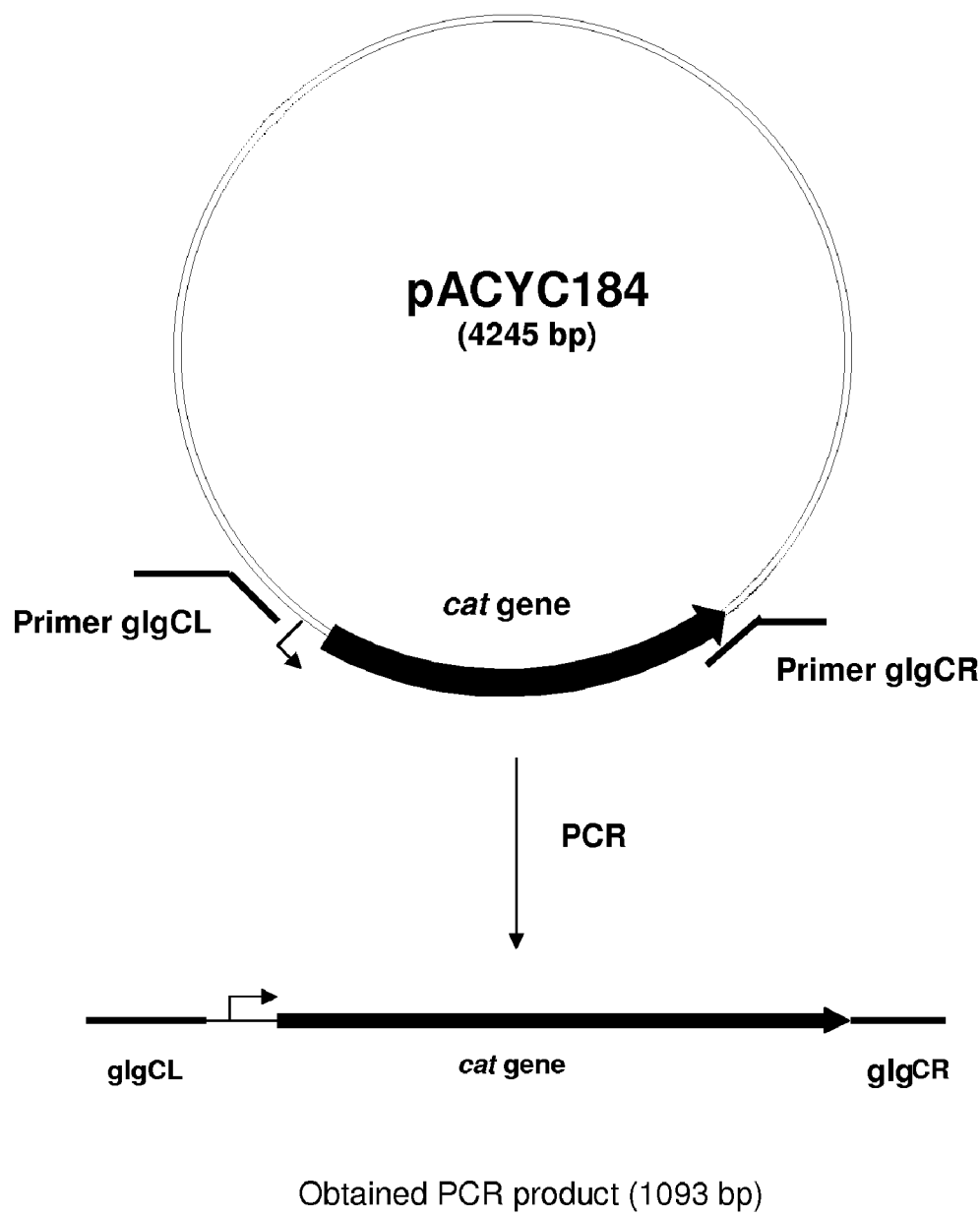
FIG. 1 shows the relative positions of primers glgCL and glgCR on plasmid pACYC184, which was used for amplification of the cat gene.

The present invention is described in detail below.

1. Bacterium of the Present Invention

The bacterium of the present invention is an L-amino acid-producing bacterium of the *Enterobacteriaceae* family, wherein the bacterium has been modified so that the glycogen biosynthesis pathway is disrupted.

In the present invention, "L-amino acid-producing bacterium" means a bacterium which has an ability to produce and excrete L-amino acid into a medium, when the bacterium is cultured in the medium.

The term "L-amino acid-producing bacterium" as used herein also means a bacterium which is able to produce and cause accumulation of an L-amino acid in a culture medium in an amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L, of the target L-amino acid. The term "L-amino acids" includes L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" comprises L-phenylalanine, L-tyrosine, and L-tryptophan. The term "non-aromatic L-amino acid" comprises L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline and L-arginine are particularly preferred.

The *Enterobacteriaceae* family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella Yersinia*, etc. Specifically, those classified into the *Enterobacteriaceae* according to the taxonomy used in the NCBI (National Center for Biotechnology Information) database (http://www.ncbi.nlm.nih.gov/htbinpost/Taxonomy/wgetorg?mode=Tree&id=1236&lvl=3&keep=1&srchmode=1&unlock) can be used. A bacterium belonging to the genus of *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified into the genus *Pantoea* according to the classification known to a person skilled in the art of microbiology. Some species of Enterobacter agglomerans have been recently re-classified into *Pantoea agglomerans*, *Pantoea ananatis*, *Pantoea stewartii* or the like on the basis of nucleotide sequence analysis of 16S rRNA, etc. (Int. J. Syst. Bacteriol., 43, 162-173 (1993)). Such strains are encompassed by "bacteria belonging to the genus *Pantoea*".

The phrase "bacterium has been modified so that the glycogen biosynthesis pathway is disrupted" means that the bacterium has been modified in such a way that the modified bacterium has a reduced ability to synthesize glycogen as compared with an unmodified bacterium or is unable to synthesize and accumulate glycogen. Disruption of glycogen biosynthetic pathway may be performed by attenuation of expression of genes encoding enzymes involved in glycogen biosynthesis, such as GlgB, GlgX, GlgC, GlgA, GlgP, and GlgS, and is preferably performed by inactivation of said genes.

The phrase "attenuation of expression of the glgBX and/or glgCAP operons" or "attenuation of expression of the glgS gene" means that the target operon or gene is modified in such a way that the modified operon or gene encodes a mutant protein(s) which has(have) a decreased activity. The phrase "inactivation of the glgBX and/or glgCAP operons" or "inactivation of the glgS gene" means that such modified operon or gene encodes a completely inactive protein(s). It is also possible that the modified DNA region is unable to naturally express the gene(s) due to the deletion of a part of the gene(s), the shifting of the reading frame of the gene(s), the introduction of missense/nonsense mutation(s), or the modification of an adjacent region of the gene(s), including sequences controlling gene expression, such as promoter(s), enhancer(s), attenuator(s), ribosome-binding site(s), etc.

The level of gene expression can be estimated by measuring the amount of mRNA transcribed from the gene using various known methods including Northern blotting, quantitative RT-PCR, and the like. The amount of the protein encoded by the gene can be measured by known methods including SDS-PAGE followed by immunoblotting assay (Western blotting analysis) and the like.

The glgC gene encodes glucose-1-phosphate adenylyltransferase (synonym—B3430). The glgC gene (gi: 16131304; nucleotides complementary to nucleotides 3566056 to 3567351 in the GenBank accession number NC_000913.2; SEQ ID NO: 1) is located between the glgA and glgX genes on the chromosome of E. coli K-12. The nucleotide sequence of the glgC gene and the amino acid sequence of the glucose-1-phosphate adenylyltransferase encoded by the glgC gene are shown in SEQ ID NO:1 and SEQ ID NO:2, respectively.

The glgA gene encodes a subunit of glycogen synthase (synonym—B3429). The glgA gene (nucleotide positions: 3,566,056 to 3,564,623; GenBank accession no. NC_000913.2; gi: 49175990) is located between the glgP and glgC genes on the chromosome of E. coli K-12. The nucleotide sequence of the glgA gene and the amino acid sequence of the subunit of glycogen synthase encoded by the glgA gene are shown in SEQ ID NO:11 and SEQ ID NO:12, respectively.

The glgP gene encodes a subunit of glycogen phosphorylase/glycogen-maltotetraose phosphorylase (synonyms—B3428, GlgY). The glgP gene (nucleotide positions: 3,564,604 to 3,562,157; GenBank accession no. NC_000913.2; gi: 49175990) is located between the yzgL and glgA genes on the chromosome of E. coli K-12. The nucleotide sequence of the glgP gene and the amino acid sequence of the subunit of glycogen phosphorylase/glycogen-maltotetraose phosphorylase encoded by the glgP gene are shown in SEQ ID NO:13 and SEQ ID NO:14, respectively.

The glgX gene encodes glycogen phosphorylase-limit dextrin α-1,6-glucohydrolase (synonyms—B3431, GlyX). The glgX gene (nucleotide positions: 3,569,342 to 3,567,369; GenBank accession no. NC_000913.2; gi: 49175990) is located between the glgC and glgB genes on the chromosome of E. coli K-12. The nucleotide sequence of the glgX gene and the amino acid sequence of the glycogen phosphorylase-limit dextrin α-1,6-glucohydrolase encoded by the glgX gene are shown in SEQ ID NO:15 and SEQ ID NO:16, respectively.

The glgB gene encodes a glycogen-branching enzyme (synonym—B3432). The glgB gene (nucleotide positions: 3,571,525 to 3,569,339; GenBank accession no. NC_000913.2; gi: 49175990) is located between the glgX and asd genes on the chromosome of E. coli K-12. The nucleotide sequence of the glgB gene and the amino acid sequence of the glycogen-branching enzyme encoded by the glgB gene are shown in SEQ ID NO:17 and SEQ ID NO:18, respectively.

The glgS gene encodes a rpoS-dependent protein of glycogen biosynthesis (synonym—B3049). The glgS gene (nucleotide positions: 3,189,961 to 3,189,761; GenBank accession no. NC_000913.2; gi: 49175990) is located between the yqiI and yqiJ ORFs on the chromosome of E. coli K-12. The nucleotide sequence of the glgS gene and the amino acid sequence of the rpoS-dependent protein of glycogen biosynthesis encoded by the glgS gene are shown in SEQ ID NO:19 and SEQ ID NO:20, respectively.

Since there may be some differences in DNA sequences between the genera or strains of the Enterobacteriaceae family, the glgC gene to be deleted on the chromosome is not limited to the gene shown in SEQ ID No:1, but may include a homologous gene of SEQ ID No:1. Therefore, the protein variant encoded by the glgC gene may have a homology of not less than 80%, preferably not less than 90%, and most preferably not less than 95%, with respect to the entire amino acid sequence encoded shown in SEQ ID NO. 2, as long as the activity of glucose-1-phosphate adenylyltransferase prior to inactivation is maintained.

Moreover, the glgC gene may be a variant which hybridizes under stringent conditions with the nucleotide sequence shown in SEQ ID NO: 1, or a probe which can be prepared from the nucleotide sequence, provided that it encodes a 1-phosphate adenylyltransferase prior to inactivation. "Stringent conditions" include those under which a specific hybrid, for example, a hybrid having homology of not less than 60%, preferably not less than 70%, more preferably not less than 80%, and still more preferably not less than 90%, and most preferably not less than 95% is formed and a non-specific hybrid, for example, a hybrid having homology lower than the above is not formed. For example, stringent conditions are exemplified by washing one time, preferably two or three times at a salt concentration corresponding to 1×SSC, 0.1% SDS, preferably 0.1×SSC, 0.1% SDS at 60° C. The length of the probe may be suitably selected depending on the hybridization conditions, and is usually 100 bp to 1 kbp.

The similar expression as described above for the glgC gene can be applied for the variants of other genes of the glgBX and glgCAP operons.

Inactivation of the gene can be performed by conventional methods, such as mutagenesis treatment using UV irradiation or nitrosoguanidine (N-methyl-N'-nitro-N-nitrosoguanidine) treatment, site-directed mutagenesis, gene disruption using homologous recombination, or/and insertion-deletion mutagenesis (Yu, D. et al., Proc. Natl. Acad. Sci. USA, 2000, 97:12: 5978-83) and (Datsenko, K. A. and Wanner, B. L., Proc. Natl. Acad. Sci. USA, 2000, 97:12: 6640-45) also called "Red-driven integration".

Activity of glucose-1-phosphate adenylyltransferase encoded by the glgC gene can be measured by the method described by, for example, Haugen, T. H. et al (J. Biol. Chem. 251 (24), 7880-5 (1976)). So, the decreasing or absent activity of glucose-1-phosphate adenylyltransferase in the bacterium according the present invention can be determined when compared to the parent unmodified bacterium.

Activity of glycogen synthase encoded by the glgA gene can be measured by the method described by, for example, Fox, J. et al (Methods Enzymol., 28, 539-544 (1972)). So, the decreasing or absent activity of glycogen synthase in the bacterium according the present invention can be determined when compared to the parent unmodified bacterium.

Activity of glycogen phosphorylase/glycogen-maltotetraose phosphorylase encoded by the glgP gene can be measured by the method described by, for example, Graves, D. J. and Wang, J. H. (The Enzymes, 7 ($3^{rd}$ ed.), 435-482 (1972)). So, the decreasing or absent activity of glycogen phosphorylase/glycogen-maltotetraose phosphorylase in the bacterium according the present invention can be determined when compared to the parent unmodified bacterium.

Activity of glycogen phosphorylase-limit dextrin α-1,6-glucohydrolase encoded by the glgX gene can be measured by the method described by, for example, Jeanningros, R. et al (Biochim Biophys Acta, 438(1), 186-199 (1976)). So, the decreasing or absent activity of glycogen phosphorylase-limit dextrin α-1,6-glucohydrolase in the bacterium according the present invention can be determined when compared to the parent unmodified bacterium.

Activity of glycogen-branching enzyme encoded by the glgB gene can be measured by the method described by, for example, Illingworth, B. B. and Brown, D. H. (Methods Enzymol., 8, 395-403 (1966)). So, the decreasing or absent activity of glycogen-branching enzyme in the bacterium according the present invention can be determined when compared to the parent unmodified bacterium.

Activity of rpoS-dependent protein of glycogen biosynthesis encoded by the glgS gene can be detected by complementation of glgS-null mutation which inhibits glycogen synthesis as described by, for example, Hengge-Aronis, R, and Fischer, D. (Mol. Microbiol., 6, 14, 1877-1886 (1992)). So, the decreasing or absent activity of rpoS dependent protein of glycogen biosynthesis in the bacterium according the present invention can be determined when compared to the parent unmodified bacterium.

Methods for preparation of plasmid DNA, digestion and ligation of DNA, transformation, selection of an oligonucleotide as a primer, and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Amino Acid-Producing Bacteria

As a bacterium of the present invention, which is modified to inactivate the glgBX and/or glgCAP operons or the glgS gene, bacteria which are able to produce either aromatic or non-aromatic L-amino acids may be used.

The bacterium of the present invention can be obtained by inactivating the glgBX and/or glgCAP operons or the glgS gene in a bacterium which inherently has the ability to produce L-amino acids. Alternatively, the bacterium of the present invention can be obtained by imparting the ability to produce L-amino acids to a bacterium already having the glgBX and/or glgCAP operons or the glgS gene inactivated.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow, 1 Dorozhny proezd., 1) on Apr. 7, 1987 under the accession number B-3996.

Preferably, the bacterium of the present invention is additionally modified to enhance expression of one or more of the following genes:

the mutant thrA gene which codes for aspartokinase homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon.

A mutant thrA gene which codes for aspartokinase homoserine dehydrogenase I resistant to feed back inhibition by threonine, as well as, the thrB and thrC genes can be obtained as one operon from well-known plasmid pVIC40 which is presented in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., *Trends Genet.*, 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346, 170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), nicotinamide adenine dinucleotide transhydrogenase (pntAB), and aspartase (aspA) (EP 1253195 A).

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase and lysine decarboxylase (U.S. Pat. No. 5,827,698).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including as β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403, 342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC⁺ (VKPM B-8961) was obtained. This strain is able to produce L-glutamic acid.

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is a strain obtained by disrupting the α-ketoglutarate dehydrogenase gene (hereinafter referred to as "sucA gene") of *E. coli* W3110. This strain is completely deficient in the α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having serA allele encoding phosphoglycerate dehydrogenase free from feedback inhibition by serine and the trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used.

Previously, it was identified that the yddG gene encoding a membrane protein, which is not involved in biosynthetic pathway of any L-amino acid, and imparts to a microorganism resistance to L-phenylalanine and several amino acid analogues when the wild-type allele of the gene was amplified on a multi-copy vector in the microorganism. Besides, the yddG gene can enhance production of L-phenylalanine or L-tryptophan when additional copies are introduced into the cells of the respective producing strain (WO03044192). So it is desirable that the L-tryptophan-producing bacterium be further modified so that expression of the yddG open reading frame is enhanced.

Examples of parent strains for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively.

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium of the present invention may be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B -12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (JP 57-5693 A), and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase.

2. Method of the Present Invention

The method of the present invention is a method for producing an L-amino acid comprising cultivating the bacterium of the present invention in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the used microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated glgC Gene

1. Deletion of the glgC Gene

A strain having deletion of the glgC gene can be constructed by the method initially developed by Datsenko, K. A. and Wanner, B. L. (Proc. Natl. Acad. Sci. USA, 2000, 97(12), 6640-6645) called "Red-driven integration". According to this procedure, the PCR primers glgCL (SEQ ID NO: 3) and glgCR (SEQ ID NO: 4) complementary to both the region adjacent to the glgC gene and the gene conferring antibiotic resistance in the template plasmid can be constructed. The plasmid pACYC184 (NBL Gene Sciences Ltd., UK) (GenBank/EMBL accession number X06403) can be used as a template in PCR reaction. Conditions for PCR can be as follows: denaturation step at 95° C. for 3 min; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1093-bp PCR product (FIG. 1) can be obtained and purified in agarose gel and can be used for electroporation of E. coli MG1655 (ATCC 700926), which contains the plasmid pKD46 having temperature-sensitive replication. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells can be prepared as follows: a night culture of E. coli MG1655 can be grown at 30° C. in LB medium supplemented with ampicillin (100 mg/l) and then diluted 100-fold with 5 ml of SOB medium (Sambrook et al, "Molecular Cloning A Laboratory Manual, Second Edition", Cold Spring Harbor Laboratory Press (1989)) containing ampicillin and L-arabinose (1 mM). The obtained culture can be grown with aeration at 30° C. to an $OD_{600}$ of ≈0.6 and then can be made electrocompetent by concentrating 100-fold and washing three times with ice-cold deionized $H_2O$. Electroporation can be performed using 70 μl of cells and ≈100 ng of the PCR product. Cells after electroporation can be incubated with 1 ml of SOC medium (Sambrook et al, "Molecular Cloning A Laboratory Manual, Second Edition", Cold Spring Harbor Laboratory Press (1989)) at 37° C. for 2.5 hours and after that can be plated onto L-agar and grown at 37° C. to select $Cm^R$ recombinants. Then, to eliminate the pKD46 plasmid, 2 passages on L-agar with Cm at 42° C. can be performed and the obtained colonies can be tested for sensitivity to ampicillin.

2. Verification of the glgC Gene Deletion by PCR

Figure 2:
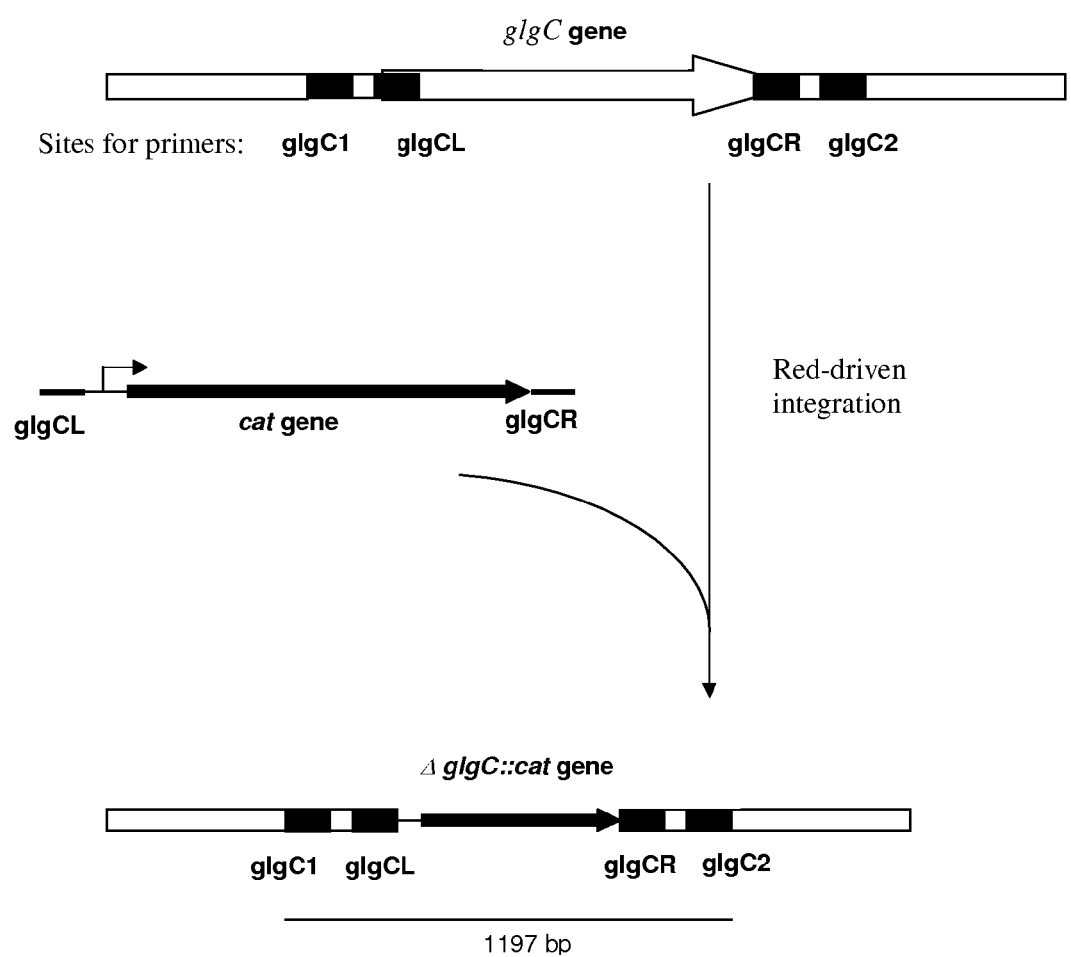
FIG. 2 shows the construction of the chromosomal DNA fragment containing the inactivated glgC gene.

The mutants, containing the deletion of the glgC gene, marked with Cm resistance gene, can be verified by PCR. Locus-specific primers glgC1 (SEQ ID NO: 5) and glgC2 (SEQ ID NO: 6) can be used in PCR for verification. Conditions for PCR verification can be as follows: denaturation step at 94° C. for 3 min; profile for the 30 cycles: 30 sec at 94° C., 30 sec at 54° C., 1 min at 72° C.; final step: 7 min at 72° C. The PCR product, which can be obtained in the reaction with the parental strain MG1655 $glgC^+$ as a template, should be 1471 bp in length. The PCR product, which can be obtained in the reaction with the mutant MG1655 ΔglgC::cat strain as a template, should be 1197 bp in length (FIG. 2).

Example 2

Production of L-Glutamate By E. coli VL334thrC$^+$-ΔglgC

The deletion of the glgC gene in the chromosome of the E. coli L-glutamate producing strain VL334thrC$^+$ (EP 1172433) can be performed by an ordinary well-known method, for example, by P1 transduction from MG1655 ΔglgC::cat strain, to obtain the strain VL334thrC$^+$-ΔglgC. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC$^+$ and VL334thrC$^+$-ΔglgC, can be grown for 18-24 hours at 37° C. on L-agar plates. Then, one loop of the cells can be transferred into test tubes containing 2 ml of a fermentation medium. The fermentation medium (pH 7.2) should contain glucose (60 g/l), ammonium sulfate (25 g/l), $KH_2PO_4$ (2 g/l), $MgSO_4$ (1 g/l), thiamine (0.1 mg/ml), L-isoleucine (70 μg/ml), and $CaCO_3$ (25 g/l). Glucose and $CaCO_3$ should be sterilized separately. Cultivation can be carried out at 30° C. for 3 days with shaking. After the cultivation, the amount of L-glutamic acid produced can be determined by paper chromatography (liquid phase composition: butanol-acetic acid-water=4:1:1) with subsequent staining by ninhydrin (1% solution in acetone) and further elution of the compounds in 50% ethanol with 0.5% $CdCl_2$.

Example 3

Production of L-Proline by E. coli 702ilvA-ΔglgC

The deletion of the glgC gene in the chromosome of the E. coli L-proline-producing strain 702ilvA (VKPM B-8012, Russian patent application 2000124295, EP1172433) can be performed by an ordinary well-known method as described above to obtain the strain 702ilvA-ΔglgC. The strain 702ilvA has been deposited in the Russian National Collection of Industrial Microorganisms (VKPM) (Russia, 117545 Moscow, 1 Dorozhny proezd, 1) on Jul. 18, 2000 under the accession number VKPM B-8012.

Both E. coli strains, 702ilvA and 702ilvA-ΔglgC, can be grown for 18-24 hours at 37° C. on L-agar plates. Then these strains can be cultivated under the same conditions as described above.

Example 4

Production of L-Arginine By E. coli 237-ΔglgC

The deletion of the glgC gene in the chromosome of the E. coli L-arginine-producing strain 237 (VKPM B-7925) can be performed by an ordinary well-known method as described above to obtain the strain 237-ΔglgC. The strain 237 has been deposited in the Russian National Collection of Industrial Microorganisms (VKPM) (Russia, 113545 Moscow, 1 Dorozhny proezd, 1) on Apr. 10, 2000 under accession number VKPM B-7925 and then converted to a deposit under the Budapest Treaty on May 18, 2001.

Both E. coli strains, 237 and 237-ΔglgC, can be grown for 18-24 hours at 37° C. on L-agar plates. Then these strains can be cultivated under the same conditions as described above.

Example 5

Production of L-Leucine By E. coli 57-ΔglgC

The deletion of the glgC gene in the chromosome of the E. coli L-leucine-producing strain 57 (VKPM B-7386, U.S. Pat. No. 6,124,121) can be performed by an ordinary well-known method as described above to obtain the strain 57-pMW-ΔglgC. The strain 57 has been deposited in the Russian National Collection of Industrial Microorganisms (VKPM) (Russia, 117545 Moscow, 1 Dorozhny proezd, 1) on May 19, 1997 under the accession number VKPM B-7386.

Both E. coli strains, 57 and 57-ΔglgC, can be grown for 18-24 hours at 37° C. on L-agar plates. Then these strains can be cultivated under the same conditions as described above without addition of isoleucine into the medium.

Example 6

Production of L-Cysteine By *E. coli* JM15(ydeD)-ΔglgC

The deletion of the glgC gene in the chromosome of the *E. coli* L-cysteine-producing strain JM15(ydeD) can be performed by an ordinary well-known method as described above to obtain the strain JM15(ydeD)-ΔglgC.

*E. coli* JM15(ydeD), a derivative of *E. coli* JM15 (U.S. Pat. No. 6,218,168), can be transformed with DNA having the ydeD gene, which encodes a membrane protein and is not involved in a biosynthetic pathway of any L-amino acid (U.S. Pat. No. 5,972,663).

Fermentation conditions for evaluation of L-cysteine production were described in detail in Example 6 of U.S. Pat. No. 6,218,168.

Example 7

Production of L-Threonine by *E. coli* B-3996-ΔglgC

The deletion of the glgC gene in the chromosome of *E. coli* L-threonine-producing strain B-3996 (VKPM B-3996) can be performed by an ordinary well-known method as described above to obtain strain B-3996-ΔglgC.

Both *E. coli* strains, B-3996 and B-3996-ΔglgC, can be grown for 18-24 hours at 37° C. on L-agar plates. Then these strains can be cultivated under the same conditions as described above.

Example 8

Production of L-Lysine By *E. coli* AJ11442-ΔglgC

The deletion of the glgC gene in the chromosome of the *E. coli* L-lysine-producing strain AJ11442 (FERM BP-1543, NRRL B-12185) can be performed by an ordinary well-known method as described above to obtain strain AJ11442-ΔglgC. The strain AJ11442 was deposited at the Fermentation Research Institute, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both *E. coli* strains, AJ11442 and AJ11442-ΔglgC, can be grown for 18-24 hours at 37° C. on L-agar plates. Then these strains can be cultivated under the same conditions as described above.

Example 9

Production of L-Phenylalanine By *E. coli* AJ12739-ΔglgC

The deletion of the glgC gene in the chromosome of the *E. coli* L-phenylalanine-producing strain AJ12739 (tyrA::Tn10, tyrR) (VKPM B-8197) can be performed by an ordinary well-known method as described above to obtain the strain AJ12739-ΔglgC. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197.

Both *E. coli* strains, AJ12739 and AJ12739-ΔglgC, can be grown for 18-24 hours at 37° C. on L-agar plates. Then these strains can be cultivated under the same conditions as described above.

Example 10

Construction of a Strain with the glgBX and glgCAP Operons Inactivated

1. Deletion of the glgBX and glgCAP Operons

A strain having deletion of the glgBX and glgCAP operons was constructed by the method initially developed by Datsenko, K. A. and Wanner, B. L. (Proc. Natl. Acad. Sci. USA, 2000, 97(12), 6640-6645) called "Red-driven integration". According to this procedure, the PCR primers glgBXCAPL (SEQ ID NO: 7) and glgBXCAPR (SEQ ID NO: 8) complementary to both the region adjacent to the glgBX and glgCAP operons and the gene conferring antibiotic resistance in the template plasmid were constructed. The plasmid pACYC184 (NBL Gene Sciences Ltd., UK) (GenBank/EMBL accession number X06403) was used as a template in PCR. Conditions for PCR were described in detail in Example 1.

A 1152-bp PCR product purified in agarose gel was used for electroporation of *E. coli* MG1655 (ATCC 700926) containing the plasmid pKD46 having temperature-sensitive replication, as described in Example 1.

2. Verification of the Deletion of the glgBX and glgCAP Operons by PCR

Figure 3:
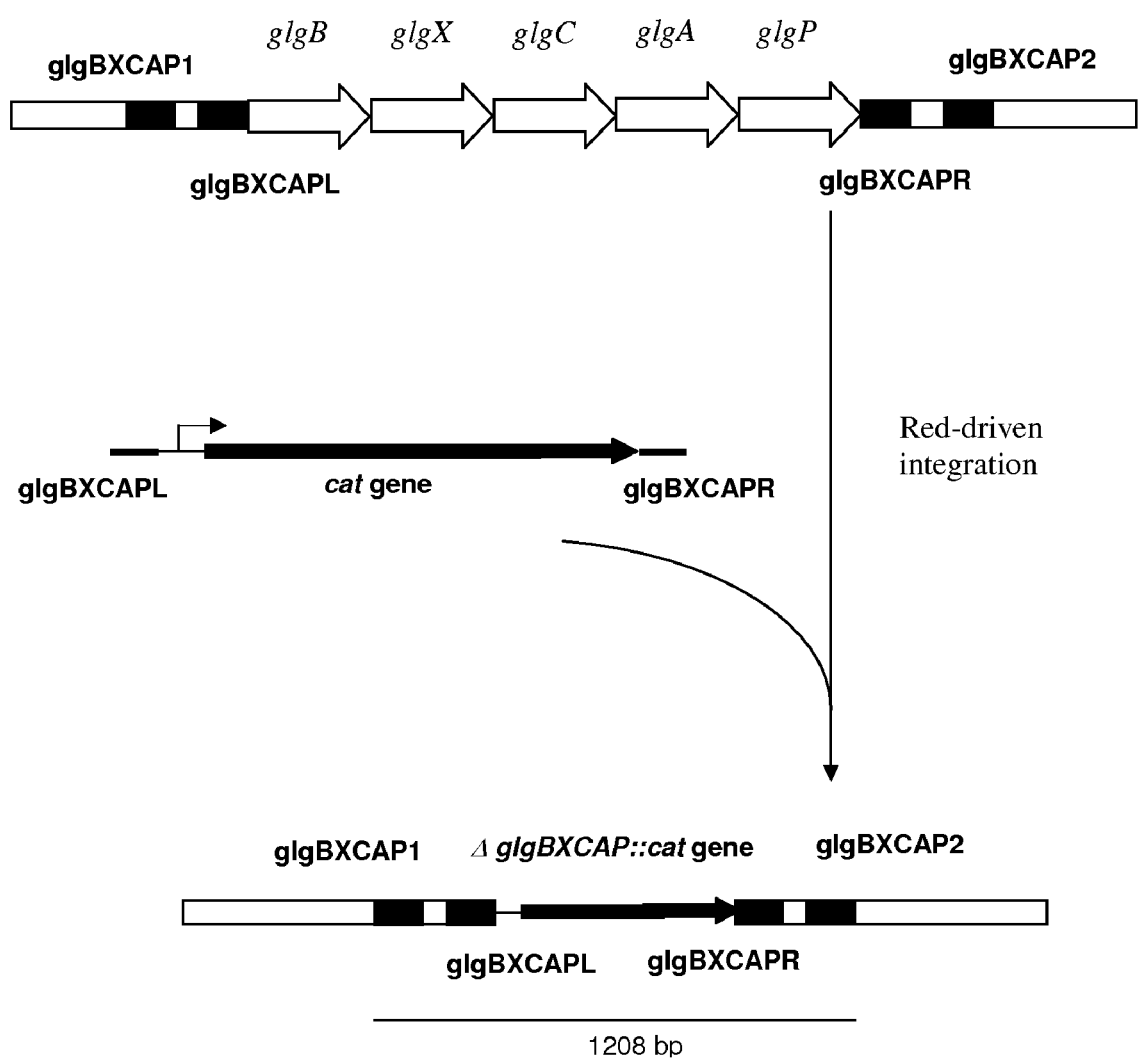
FIG. 3 shows the construction of the chromosomal DNA fragment containing the inactivated glgBX and glgCAP operons.

The mutants containing the deletion of the glgBX and glgCAP operons and marked with Cm resistance gene were verified by PCR. Locus-specific primers glgBXCAP1 (SEQ ID NO: 9) and glgBXCAP2 (SEQ ID NO: 10) were used in PCR for the verification. Conditions for PCR verification were described in Example 1. The PCR product obtained in the reaction with the parental strain MG1655 glgBXCAP⁺ as a template was 9425 bp in length. The PCR product obtained in the reaction with the mutant strain MG1655 ΔglgBXCAP::cat as a template was 1208 bp in length (FIG. 3).

Example 11

Production of L-Threonine By *E. coli* Strain B-3996-ΔglgBXCAP

To test the effect of inactivation of the glgBX and glgCAP operons on threonine production, DNA fragments from the chromosome of the above-described *E. coli* strain MG1655 ΔglgBXCAP::cat were transferred to the threonine-producing *E. coli* strain B-3996 by P1 transduction (Miller, J. H. Experiments in Molecular Genetics, Cold Spring Harbor Lab. Press, 1972, Plainview, N.Y.).

Both *E. coli* strains, B-3996 and B-3996-ΔglgBXCAP, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine accumulated in the medium was determined by paper chromatography using the following mobile phase: butanol—acetic acid—water=4:1:1 (v/v). A solution of ninhydrin (2%) in acetone was used as a visualizing reagent. A spot containing L-threonine was cut off, L-threonine was eluted with 0.5% water solution of $CdCl_2$, and the amount of L-threonine was estimated spectrophotometrically at 540 nm. The results of ten independent test-tube fermentations are shown in Table 1.

The composition of the fermentation medium (g/l) was as follows:

| | | |
|---|---|---|
| | Glucose | 80.0 |
| | $(NH_4)_2SO_4$ | 22.0 |
| | NaCl | 0.8 |
| | $KH_2PO_4$ | 2.0 |
| | $MgSO_4 \cdot 7H_2O$ | 0.8 |
| | $FeSO_4 \cdot 7H_2O$ | 0.02 |
| | $MnSO_4 \cdot 5H_2O$ | 0.02 |
| | Thiamine HCl | 0.0002 |
| | Yeast extract | 1.0 |
| | $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was added to the medium after sterilization.

As follows from Table 1, B-3996-ΔglgBXCAP caused accumulation of a higher amount of L-threonine, as compared with B-3996.

Example 12

Production of L-Lysine By *E. coli* WC196-ΔglgBXCAP

To test the effect of inactivation of the glgBX and glgCAP operons on L-lysine production, DNA fragments from the chromosome of the above-described *E. coli* strain MG1655 ΔglgBXCAP::cat were transferred to the L-lysine producing *E. coli* strain WC196 (FERM BP-5252) by P1 transduction (Miller, J. H. Experiments in Molecular Genetics, Cold Spring Harbor Lab. Press, 1972, Plainview, N.Y.).

To obtain a seed culture, both *E. coli* strains, WC196 and WC196-ΔglgBXCAP, were grown on a rotary shaker (250 rpm) at 32° C. for 18 hours in 20×200-mm test tubes containing 2 ml of medium diluted two times compare to the fermentation medium described below. Then the fermentation medium was inoculated with 0.21 ml (10%) of seed material. The fermentation was performed in 2 ml of minimal medium for fermentation in 20×200-mm test tubes. Cells were grown for 24 hours at 32° C. with shaking at 250 rpm.

After cultivation, the amount of L-lysine accumulated in the medium was determined by paper chromatography using the following mobile phase: butanol—acetic acid—water=4:1:1 (v/v). A solution of ninhydrin (2%) in acetone was used as a visualizing reagent. A spot containing L-lysine was cut off, L-lysine was eluted with 0.5% water solution of $CdCl_2$, and the amount of L-lysine was estimated spectrophotometrically at 540 nm. The results of ten independent test-tube fermentations are shown in Table 2.

The composition of the fermentation medium (g/l) was as follows:

| | | |
|---|---|---|
| | Glucose | 40.0 |
| | $(NH_4)_2SO_4$ | 24.0 |
| | $KH_2PO_4$ | 1.0 |
| | $MgSO_4 \cdot 7H_2O$ | 1.0 |
| | $FeSO_4 \cdot 7H_2O$ | 0.01 |
| | $MnSO_4 \cdot 5H_2O$ | 0.01 |
| | Yeast extract | 2.0 |
| | $CaCO_3$ | 30.0 |

Glucose, potassium phosphate and magnesium sulfate were sterilized separately. $CaCO_3$ was sterilized by dry-heat at 180° C. for 2 hours. The pH was adjusted to 7.0.

As follows from Table 2, WC196-ΔglgBXCAP caused accumulation of a higher amount of L-lysine, as compared with WC196.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

TABLE 1

| Strain | $OD_{540}$ | Amount of L-threonine, g/l |
|---|---|---|
| B-3996 | 23.5 ± 0.3 | 27.5 ± 0.4 |
| B-3996-ΔglgBXCAP | 22.1 ± 0.2 | 28.2 ± 1.2 |

TABLE 2

| Strain | $OD_{540}$ | Amount of L-lysine, g/l |
|---|---|---|
| WC196 | 26.2 ± 0.5 | 2.1 ± 0.1 |
| WC196-ΔglgBXCAP | 26.9 ± 0.3 | 2.4 ± 0.1 |

INDUSTRIAL APPLICABILITY

According to the present invention, production of an aromatic L-amino acid or a non-aromatic L-amino acid of a bacterium of the *Enterobacteriaceae* family can be enhanced.

We claim:

1. An *Escherichia coli* bacterium which is able to produce L-threonine or L-lysine and which has been modified so that the glycogen biosynthetic pathway is disrupted by attenuation of expression of the glgBX and glgCAP operons.

2. The bacterium according to claim 1, wherein said glycogen biosynthetic pathway is disrupted by inactivation of the glgBX and/or glgCAP operons.

3. The bacterium according to claim 2, wherein the inactivation of the glgBX and/or glgCAP operons comprises deletion of a gene selected from the group consisting of glgB, glgX glgC, glgA, glgP, and combinations thereof.

4. The bacterium according to claim 1, wherein said glycogen biosynthetic pathway is disrupted by attenuation of expression of the glgS gene.

5. The bacterium according to claim 1, wherein said glycogen biosynthetic pathway is disrupted by inactivation of the glgS gene.

6. A method for producing L-amino acid selected from the group consisting of L-threonine. L-lysine, and combinations thereof, comprising:
    cultivating the bacterium according to claim 1 in a medium to produce and excrete said L-amino acid into the medium, and
    collecting said L-amino acid from the medium.

7. A method for producing an L-amino acid selected from the group consisting of L-threonine, L-lysine, and combinations thereof, comprising:
    cultivating the bacterium according to claim 2 in a medium to produce and excrete said L-amino acid into the medium, and
    collecting said L-amino acid from the medium.

8. A method for producing an L-amino acid selected from the group consisting of L-threonine, L-lysine, and combinations thereof, comprising:
    cultivating the bacterium according to claim 3 in a medium to produce and excrete said L-amino acid into the medium, and
    collecting said L-amino acid from the medium.

9. A method for producing an L-amino acid selected from the group consisting of L-threonine, L-lysine, and combinations thereof, comprising:
    cultivating the bacterium according to claim 4 in a medium to produce and excrete said L-amino acid into the medium, and
    collecting said L-amino acid from said medium.

10. A method for producing an L-amino acid selected from the group consisting of L-threonine, L-lysine, and combinations thereof, comprising:
    cultivating the bacterium according to claim 5 in a medium to produce and excrete said L-amino acid into the medium, and
    collecting said L-amino acid from the medium.

* * * * *

SEQUENCE LISTING

<160> NUMBER OF SEQ ID NOS: 20

<210> SEQ ID NO 1
<211> LENGTH: 1296
<212> TYPE: DNA
<213> ORGANISM: Escherichia coli
<220> FEATURE:
<221> NAME/KEY: CDS
<222> LOCATION: (1)..(1296)

<400> SEQUENCE: 1

| | | | | | | | | | | | | | | | | |
|---|---|---|---|---|---|---|---|---|---|---|---|---|---|---|---|---|
| atg | gtt | agt | tta | gag | aag | aac | gat | cac | tta | atg | ttg | gcg | cgc | cag | ctg | 48 |
| Met | Val | Ser | Leu | Glu | Lys | Asn | Asp | His | Leu | Met | Leu | Ala | Arg | Gln | Leu | |
| 1 | | | | 5 | | | | | 10 | | | | | 15 | | |
| cca | ttg | aaa | tct | gtt | gcc | ctg | ata | ctg | gcg | gga | gga | cgt | ggt | acc | cgc | 96 |
| Pro | Leu | Lys | Ser | Val | Ala | Leu | Ile | Leu | Ala | Gly | Gly | Arg | Gly | Thr | Arg | |
| | | | 20 | | | | | 25 | | | | | 30 | | | |
| ctg | aag | gat | tta | acc | aat | aag | cga | gca | aaa | ccg | gcc | gta | cac | ttc | ggc | 144 |
| Leu | Lys | Asp | Leu | Thr | Asn | Lys | Arg | Ala | Lys | Pro | Ala | Val | His | Phe | Gly | |
| | | | 35 | | | | | 40 | | | | | 45 | | | |
| ggt | aag | ttc | cgc | att | atc | gac | ttt | gcg | ctg | tct | aac | tgc | atc | aac | tcc | 192 |
| Gly | Lys | Phe | Arg | Ile | Ile | Asp | Phe | Ala | Leu | Ser | Asn | Cys | Ile | Asn | Ser | |
| | 50 | | | | | 55 | | | | | 60 | | | | | |
| ggg | atc | cgt | cgt | atg | ggc | gtg | atc | acc | cag | tac | cag | tcc | cac | act | ctg | 240 |
| Gly | Ile | Arg | Arg | Met | Gly | Val | Ile | Thr | Gln | Tyr | Gln | Ser | His | Thr | Leu | |
| 65 | | | | | 70 | | | | | 75 | | | | | 80 | |
| gtg | cag | cac | att | cag | cgc | ggc | tgg | tca | ttc | ttc | aat | gaa | gaa | atg | aac | 288 |
| Val | Gln | His | Ile | Gln | Arg | Gly | Trp | Ser | Phe | Phe | Asn | Glu | Glu | Met | Asn | |
| | | | | 85 | | | | | 90 | | | | | 95 | | |
| gag | ttt | gtc | gat | ctg | ctg | cca | gca | cag | cag | aga | atg | aaa | ggg | gaa | aac | 336 |
| Glu | Phe | Val | Asp | Leu | Leu | Pro | Ala | Gln | Gln | Arg | Met | Lys | Gly | Glu | Asn | |
| | | | 100 | | | | | 105 | | | | | 110 | | | |
| tgg | tat | cgc | ggc | acc | gca | gat | gcg | gtc | acc | caa | aac | ctc | gac | att | atc | 384 |
| Trp | Tyr | Arg | Gly | Thr | Ala | Asp | Ala | Val | Thr | Gln | Asn | Leu | Asp | Ile | Ile | |
| | | | 115 | | | | | 120 | | | | | 125 | | | |
| cgc | cgt | tat | aaa | gcg | gaa | tac | gtg | gtg | atc | ctg | gcg | ggc | gac | cat | atc | 432 |
| Arg | Arg | Tyr | Lys | Ala | Glu | Tyr | Val | Val | Ile | Leu | Ala | Gly | Asp | His | Ile | |
| | 130 | | | | | 135 | | | | | 140 | | | | | |
| tac | aag | caa | gac | tac | tcg | cgt | atg | ctt | atc | gat | cac | gtc | gaa | aaa | ggc | 480 |
| Tyr | Lys | Gln | Asp | Tyr | Ser | Arg | Met | Leu | Ile | Asp | His | Val | Glu | Lys | Gly | |
| 145 | | | | | 150 | | | | | 155 | | | | | 160 | |
| gca | cgt | tgc | acc | gtt | gct | tgt | atg | cca | gta | ccg | att | gaa | gaa | gcc | tcc | 528 |
| Ala | Arg | Cys | Thr | Val | Ala | Cys | Met | Pro | Val | Pro | Ile | Glu | Glu | Ala | Ser | |
| | | | | 165 | | | | | 170 | | | | | 175 | | |
| gca | ttt | ggc | gtt | atg | gcg | gtt | gat | gag | aac | gat | aaa | att | atc | gaa | ttc | 576 |
| Ala | Phe | Gly | Val | Met | Ala | Val | Asp | Glu | Asn | Asp | Lys | Ile | Ile | Glu | Phe | |
| | | | 180 | | | | | 185 | | | | | 190 | | | |
| gtt | gaa | aaa | cct | gct | aac | ccg | ccg | tca | atg | ccg | aac | gat | ccg | agc | aaa | 624 |
| Val | Glu | Lys | Pro | Ala | Asn | Pro | Pro | Ser | Met | Pro | Asn | Asp | Pro | Ser | Lys | |
| | | | 195 | | | | | 200 | | | | | 205 | | | |
| tct | ctg | gcg | agt | atg | ggt | atc | tac | gtc | ttt | gac | gcc | gac | tat | ctg | tat | 672 |
| Ser | Leu | Ala | Ser | Met | Gly | Ile | Tyr | Val | Phe | Asp | Ala | Asp | Tyr | Leu | Tyr | |
| | | | 210 | | | | | 215 | | | | | 220 | | | |
| gaa | ctg | ctg | gaa | gaa | gac | gat | cgc | gat | gag | aac | tcc | agc | cac | gac | ttt | 720 |
| Glu | Leu | Leu | Glu | Glu | Asp | Asp | Arg | Asp | Glu | Asn | Ser | Ser | His | Asp | Phe | |
| 225 | | | | | 230 | | | | | 235 | | | | | 240 | |
| ggc | aaa | gat | ttg | att | ccc | aag | atc | acc | gaa | gcc | ggt | ctg | gcc | tat | gcg | 768 |
| Gly | Lys | Asp | Leu | Ile | Pro | Lys | Ile | Thr | Glu | Ala | Gly | Leu | Ala | Tyr | Ala | |
| | | | 245 | | | | | 250 | | | | | 255 | | | |
| cac | ccg | ttc | ccg | ctc | tct | tgc | gta | caa | tcc | gac | ccg | gat | gcc | gag | ccg | 816 |
| His | Pro | Phe | Pro | Leu | Ser | Cys | Val | Gln | Ser | Asp | Pro | Asp | Ala | Glu | Pro | |
| | | | 260 | | | | | 265 | | | | | 270 | | | |
| tac | tgg | cgc | gat | gtg | ggt | acg | ctg | gaa | gct | tac | tgg | aaa | gcg | aac | ctc | 864 |
| Tyr | Trp | Arg | Asp | Val | Gly | Thr | Leu | Glu | Ala | Tyr | Trp | Lys | Ala | Asn | Leu | |
| | | | 275 | | | | | 280 | | | | | 285 | | | |
| gat | ctg | gcc | tct | gtg | gtg | ccg | gaa | ctg | gat | atg | tac | gat | cgc | aat | tgg | 912 |
| Asp | Leu | Ala | Ser | Val | Val | Pro | Glu | Leu | Asp | Met | Tyr | Asp | Arg | Asn | Trp | |
| | | | 290 | | | | | 295 | | | | | 300 | | | |

| | | |
|---|---|---|
| cca att cgc acc tac aat gaa tca tta ccg cca gcg aaa ttc gtg cag<br>Pro Ile Arg Thr Tyr Asn Glu Ser Leu Pro Pro Ala Lys Phe Val Gln<br>305                       310                     315                   320 | 960 |
| gat cgc tcc ggt agc cac ggg atg acc ctt aac tca ctg gtt tcc ggc<br>Asp Arg Ser Gly Ser His Gly Met Thr Leu Asn Ser Leu Val Ser Gly<br>                  325                   330                   335 | 1008 |
| ggt tgt gtg atc tcc ggt tcg gtg gtg gtg cag tcc gtt ctg ttc tcg<br>Gly Cys Val Ile Ser Gly Ser Val Val Val Gln Ser Val Leu Phe Ser<br>        340                   345                   350 | 1056 |
| cgc gtt cgc gtg aat tca ttc tgc aac att gat tcc gcc gta ttg tta<br>Arg Val Arg Val Asn Ser Phe Cys Asn Ile Asp Ser Ala Val Leu Leu<br>               355                   360                   365 | 1104 |
| ccg gaa gta tgg gta ggt cgc tcg tgc cgt ctg cgc cgc tgc gtc atc<br>Pro Glu Val Trp Val Gly Arg Ser Cys Arg Leu Arg Arg Cys Val Ile<br>370                       375                     380 | 1152 |
| gat cgt gct tgt gtt att ccg gaa ggc atg gtg att ggt gaa aac gca<br>Asp Arg Ala Cys Val Ile Pro Glu Gly Met Val Ile Gly Glu Asn Ala<br>385                       390                     395                   400 | 1200 |
| gag gaa gat gca cgt cgt ttc tat cgt tca gaa gaa ggc atc gtg ctg<br>Glu Glu Asp Ala Arg Arg Phe Tyr Arg Ser Glu Glu Gly Ile Val Leu<br>                  405                   410                   415 | 1248 |
| gta acg cgc gaa atg cta cgg aag tta ggg cat aaa cag gag cga taa<br>Val Thr Arg Glu Met Leu Arg Lys Leu Gly His Lys Gln Glu Arg<br>        420                   425                   430 | 1296 |

<210> SEQ ID NO 2
<211> LENGTH: 431
<212> TYPE: PRT
<213> ORGANISM: Escherichia coli

<400> SEQUENCE: 2

Met Val Ser Leu Glu Lys Asn Asp His Leu Met Leu Ala Arg Gln Leu
1                 5                   10                   15

Pro Leu Lys Ser Val Ala Leu Ile Leu Ala Gly Gly Arg Gly Thr Arg
              20                   25                   30

Leu Lys Asp Leu Thr Asn Lys Arg Ala Lys Pro Ala Val His Phe Gly
            35                   40                   45

Gly Lys Phe Arg Ile Ile Asp Phe Ala Leu Ser Asn Cys Ile Asn Ser
    50                   55                   60

Gly Ile Arg Arg Met Gly Val Ile Thr Gln Tyr Gln Ser His Thr Leu
65                70                   75                   80

Val Gln His Ile Gln Arg Gly Trp Ser Phe Phe Asn Glu Glu Met Asn
                85                   90                   95

Glu Phe Val Asp Leu Leu Pro Ala Gln Gln Arg Met Lys Gly Glu Asn
            100                105                110

Trp Tyr Arg Gly Thr Ala Asp Ala Val Thr Gln Asn Leu Asp Ile Ile
        115                120                125

Arg Arg Tyr Lys Ala Glu Tyr Val Val Ile Leu Ala Gly Asp His Ile
    130                  135                140

Tyr Lys Gln Asp Tyr Ser Arg Met Leu Ile Asp His Val Glu Lys Gly
145              150                 155                160

Ala Arg Cys Thr Val Ala Cys Met Pro Val Pro Ile Glu Glu Ala Ser
               165                170                175

Ala Phe Gly Val Met Ala Val Asp Glu Asn Asp Lys Ile Ile Glu Phe
        180                185                190

Val Glu Lys Pro Ala Asn Pro Pro Ser Met Pro Asn Asp Pro Ser Lys
    195                  200                205

-continued

Ser Leu Ala Ser Met Gly Ile Tyr Val Phe Asp Ala Asp Tyr Leu Tyr
    210                 215                 220

Glu Leu Leu Glu Glu Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Gly Ile Val Leu
                405                 410                 415

Val Thr Arg Glu Met Leu Arg Lys Leu Gly His Lys Gln Glu Arg
        420                 425                 430

<210> SEQ ID NO 3
<211> LENGTH: 59
<212> TYPE: DNA
<213> ORGANISM: Artificial
<220> FEATURE:
<223> OTHER INFORMATION: primer

<400> SEQUENCE: 3
gtgtgtgttc cagagatgat aaaaaaggag ttagtctgat gtccggcggt gcttttgcc    59

<210> SEQ ID NO 4
<211> LENGTH: 57
<212> TYPE: DNA
<213> ORGANISM: Artificial
<220> FEATURE:
<223> OTHER INFORMATION: primer

<400> SEQUENCE: 4
cgggaacatc tctgaacata catgtaaaac ctgcatttac gccccgccct gccactc    57

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
ataacccagt gattacggct gtc    23

```
<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
cgatttgtgc tgcgggtaat g                                              21

<210> SEQ ID NO 7
<211> LENGTH: 57
<212> TYPE: DNA
<213> ORGANISM: Artificial
<220> FEATURE:
<223> OTHER INFORMATION: primer

<400> SEQUENCE: 7
atgtccgatc gtatcgatag agacgtgatt aacgcgtagt aagccagtat acactcc       57

<210> SEQ ID NO 8
<211> LENGTH: 57
<212> TYPE: DNA
<213> ORGANISM: Artificial
<220> FEATURE:
<223> OTHER INFORMATION: primer

<400> SEQUENCE: 8
ttacaatctc accggatcga tatgccagat atgatcttaa gggcaccaat aactgcc       57

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
ggggtgacac aataaaacag g                                              21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tggccccgtt ctatttattg g                                              21

<210> SEQ ID NO 11
<211> LENGTH: 1434
<212> TYPE: DNA
<213> ORGANISM: Escherichia coli
<220> FEATURE:
<221> NAME/KEY: CDS
<222> LOCATION: (1)..(1434)

<400> SEQUENCE: 11 atg cag gtt tta cat gta tgt tca gag atg ttc ccg ctg ctt aaa acc      48
Met Gln Val Leu His Val Cys Ser Glu Met Phe Pro Leu Leu Lys Thr
1               5                   10                  15 ggc ggt ctg gct gat gtt att ggg gca tta ccc gca gca caa atc gca      96
Gly Gly Leu Ala Asp Val Ile Gly Ala Leu Pro Ala Ala Gln Ile Ala
            20                  25                  30 gac ggc gtt gac gct cgc gta ctg ttg cct gca ttt ccc gat att cgc     144
Asp Gly Val Asp Ala Arg Val Leu Leu Pro Ala Phe Pro Asp Ile Arg
```

```
                                                            -continued

Asp Gly Val Asp Ala Arg Val Leu Leu Pro Ala Phe Pro Asp Ile Arg
         35                  40                  45 cgt ggc gtg acc gat gcg cag gta gta tcc cgt cgt gat acc ttc gcc      192
Arg Gly Val Thr Asp Ala Gln Val Val Ser Arg Arg Asp Thr Phe Ala
     50                  55                  60 gga cat atc acg ctg ttg ttc ggt cat tac aac ggg gtt ggc att tac      240
Gly His Ile Thr Leu Leu Phe Gly His Tyr Asn Gly Val Gly Ile Tyr
65                  70                  75                  80 ctg att gac gcg ccg cat ctc tat gat cgt ccg gga agc ccg tat cac      288
Leu Ile Asp Ala Pro His Leu Tyr Asp Arg Pro Gly Ser Pro Tyr His
                 85                  90                  95 gat acc aac tta ttt gcc tat acc gac aac gta ttg cgt ttt gcg ctg      336
Asp Thr Asn Leu Phe Ala Tyr Thr Asp Asn Val Leu Arg Phe Ala Leu
        100                 105                 110 ctg ggg tgg gtt ggg gca gaa atg gcc agc ggg ctt gac cca ttc tgg      384
Leu Gly Trp Val Gly Ala Glu Met Ala Ser Gly Leu Asp Pro Phe Trp
            115                 120                 125 cgt cct gat gtg gtg cat gcg cac gac tgg cat gca ggc ctt gcg cct      432
Arg Pro Asp Val Val His Ala His Asp Trp His Ala Gly Leu Ala Pro
        130                 135                 140 gcg tat ctg gcg gcg cgc ggg cgt ccg gcg aag tcg gtg ttt act gtg      480
Ala Tyr Leu Ala Ala Arg Gly Arg Pro Ala Lys Ser Val Phe Thr Val
145                 150                 155                 160 cac aac ctg gcc tat caa ggc atg ttt tat gca cat cac atg aat gac      528
His Asn Leu Ala Tyr Gln Gly Met Phe Tyr Ala His His Met Asn Asp
                165                 170                 175 atc caa ttg cca tgg tca ttc ttt aat att cat ggg ctg gaa ttc aac      576
Ile Gln Leu Pro Trp Ser Phe Phe Asn Ile His Gly Leu Glu Phe Asn
            180                 185                 190 gga caa atc tct ttc ctg aag gcc ggt ctg tac tat gcc gat cac att      624
Gly Gln Ile Ser Phe Leu Lys Ala Gly Leu Tyr Tyr Ala Asp His Ile
        195                 200                 205 acg gcg gtc agt cca acc tac gct cgc gag atc acc gaa ccg cag ttt      672
Thr Ala Val Ser Pro Thr Tyr Ala Arg Glu Ile Thr Glu Pro Gln Phe
210                 215                 220 gcc tac ggt atg gaa ggt ctg ttg caa cag cgt cac cgt gaa ggg cgt      720
Ala Tyr Gly Met Glu Gly Leu Leu Gln Gln Arg His Arg Glu Gly Arg
225                 230                 235                 240 ctt tcc ggc gta ctg aac ggc gtg gac gag aaa atc tgg agt cca gag      768
Leu Ser Gly Val Leu Asn Gly Val Asp Glu Lys Ile Trp Ser Pro Glu
                245                 250                 255 acg gac tta ctg ttg gcc tcg cgt tac acc cgc gat acg ttg gaa gat      816
Thr Asp Leu Leu Leu Ala Ser Arg Tyr Thr Arg Asp Thr Leu Glu Asp
            260                 265                 270 aaa gcg gaa aat aag cgc cag tta caa atc gca atg ggg ctt aag gtt      864
Lys Ala Glu Asn Lys Arg Gln Leu Gln Ile Ala Met Gly Leu Lys Val
        275                 280                 285 gac gat aaa gtg ccg ctt ttt gca gtg gtg agc cgt ctg acc agc cag      912
Asp Asp Lys Val Pro Leu Phe Ala Val Val Ser Arg Leu Thr Ser Gln
290                 295                 300 aaa ggt ctc gac ctg gtg ctg gaa gcc tta ccg ggt ctt ctg gag cag      960
Lys Gly Leu Asp Leu Val Leu Glu Ala Leu Pro Gly Leu Leu Glu Gln
305                 310                 315                 320 ggc ggg cag ctg gcg cta ctc ggc gcg ggc gat ccg gtg ctg cag gaa     1008
Gly Gly Gln Leu Ala Leu Leu Gly Ala Gly Asp Pro Val Leu Gln Glu
                325                 330                 335 ggt ttc ctt gcg gcg gca gcg gaa tac ccc ggt cag gtg ggc gtt cag     1056
Gly Phe Leu Ala Ala Ala Ala Glu Tyr Pro Gly Gln Val Gly Val Gln
            340                 345                 350
```

```
att ggc tat cac gaa gca ttt tcg cat cgc att atg ggc ggc gcg gac    1104
Ile Gly Tyr His Glu Ala Phe Ser His Arg Ile Met Gly Gly Ala Asp
        355                 360                 365 gtc att ctg gtg ccc agc cgt ttt gaa ccg tgc ggc tta acg caa ctt    1152
Val Ile Leu Val Pro Ser Arg Phe Glu Pro Cys Gly Leu Thr Gln Leu
370                 375                 380 tat gga ttg aag tac ggt acg ctg ccg tta gtg cgg cgc acc ggt ggg    1200
Tyr Gly Leu Lys Tyr Gly Thr Leu Pro Leu Val Arg Arg Thr Gly Gly
385                 390                 395                 400 ctt gct gat acg gtt tct gac tgt tct ctt gag aac ctt gca gat ggc    1248
Leu Ala Asp Thr Val Ser Asp Cys Ser Leu Glu Asn Leu Ala Asp Gly
        405                 410                 415 gtc gcc agt ggg ttt gtc ttt gaa gat agt aat gcc tgg tcg ctg tta    1296
Val Ala Ser Gly Phe Val Phe Glu Asp Ser Asn Ala Trp Ser Leu Leu
        420                 425                 430 cgg gct att cga cgt gct ttt gta ctg tgg tcc cgt cct tca ctg tgg    1344
Arg Ala Ile Arg Arg Ala Phe Val Leu Trp Ser Arg Pro Ser Leu Trp
        435                 440                 445 cgg ttt gtg caa cgt cag gct atg gca atg gat ttt agc tgg cag gtc    1392
Arg Phe Val Gln Arg Gln Ala Met Ala Met Asp Phe Ser Trp Gln Val
450                 455                 460 gcg gcg aag tcg tac cgt gag ctt tac tat cgc ttg aaa tag            1434
Ala Ala Lys Ser Tyr Arg Glu Leu Tyr Tyr Arg Leu Lys
465                 470                 475

<210> SEQ ID NO 12
<211> LENGTH: 477
<212> TYPE: PRT
<213> ORGANISM: Escherichia coli

<400> SEQUENCE: 12

Met Gln Val Leu His Val Cys Ser Glu Met Phe Pro Leu Leu Lys Thr
1               5                   10                  15

Gly Gly Leu Ala Asp Val Ile Gly Ala Leu Pro Ala Ala Gln Ile Ala
            20                  25                  30

Asp Gly Val Asp Ala Arg Val Leu Leu Pro Ala Phe Pro Asp Ile Arg
        35                  40                  45

Arg Gly Val Thr Asp Ala Gln Val Val Ser Arg Arg Asp Thr Phe Ala
    50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
            100                 105                 110

Leu Gly Trp Val Gly Ala Glu Met Ala Ser Gly Leu Asp Pro Phe Trp
        115                 120                 125

Arg Pro Asp Val Val His Ala His Asp Trp His Ala Gly Leu Ala Pro
    130                 135                 140

Ala Tyr Leu Ala Ala Arg Gly Arg Pro Ala Lys Ser Val Phe Thr Val
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
            180                 185                 190

Gly Gln Ile Ser Phe Leu Lys Ala Gly Leu Tyr Tyr Ala Asp His Ile
        195                 200                 205
```

```
Thr Ala Val Ser Pro Thr Tyr Ala Arg Glu Ile Thr Glu Pro Gln Phe
    210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
                260                 265                 270

Lys Ala Glu Asn Lys Arg Gln Leu Gln Ile Ala Met Gly Leu Lys Val
                275                 280                 285

Asp Asp Lys Val Pro Leu Phe Ala Val Val Ser Arg Leu Thr Ser Gln
    290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
                325                 330                 335

Gly Phe Leu Ala Ala Ala Ala Glu Tyr Pro Gly Gln Val Gly Val Gln
                340                 345                 350

Ile Gly Tyr His Glu Ala Phe Ser His Arg Ile Met Gly Gly Ala Asp
                355                 360                 365

Val Ile Leu Val Pro Ser Arg Phe Glu Pro Cys Gly Leu Thr Gln Leu
    370                 375                 380

Tyr Gly Leu Lys Tyr Gly Thr Leu Pro Leu Val Arg Arg Thr Gly Gly
385                 390                 395                 400

Leu Ala Asp Thr Val Ser Asp Cys Ser Leu Glu Asn Leu Ala Asp Gly
                405                 410                 415

Val Ala Ser Gly Phe Val Phe Glu Asp Ser Asn Ala Trp Ser Leu Leu
                420                 425                 430

Arg Ala Ile Arg Arg Ala Phe Val Leu Trp Ser Arg Pro Ser Leu Trp
                435                 440                 445

Arg Phe Val Gln Arg Gln Ala Met Ala Met Asp Phe Ser Trp Gln Val
    450                 455                 460

Ala Ala Lys Ser Tyr Arg Glu Leu Tyr Tyr Arg Leu Lys
465                 470                 475

<210> SEQ ID NO 13
<211> LENGTH: 2448
<212> TYPE: DNA
<213> ORGANISM: Escherichia coli
<220> FEATURE:
<221> NAME/KEY: CDS
<222> LOCATION: (1)..(2448)

<400> SEQUENCE: 13 atg aat gct ccg ttt aca tat tca tcg ccc acg ctt agc gta gaa gct     48
Met Asn Ala Pro Phe Thr Tyr Ser Ser Pro Thr Leu Ser Val Glu Ala
1               5                   10                  15 ctt aag cac tct atc gct tac aag ctg atg ttt acg att gga aag gac     96
Leu Lys His Ser Ile Ala Tyr Lys Leu Met Phe Thr Ile Gly Lys Asp
            20                  25                  30 ccg gtc gtc gcc aat aaa cat gaa tgg ctg aac gca acg tta ttt gct    144
Pro Val Val Ala Asn Lys His Glu Trp Leu Asn Ala Thr Leu Phe Ala
        35                  40                  45 gtg cgc gat cgt ctc gtg gag cgc tgg tta cgt tca aac cgt gcc cag    192
Val Arg Asp Arg Leu Val Glu Arg Trp Leu Arg Ser Asn Arg Ala Gln
    50                  55                  60 ttg tcg caa gaa act cgt cag gtt tac tac ctg tcg atg gag ttt ttg    240
```

```
Leu Ser Gln Glu Thr Arg Gln Val Tyr Tyr Leu Ser Met Glu Phe Leu
65              70                  75                  80 att ggc cgt acg ctc tcc aac gcc atg ttg tcg cta gga att tac gaa        288
Ile Gly Arg Thr Leu Ser Asn Ala Met Leu Ser Leu Gly Ile Tyr Glu
                85                  90                  95 gat gta cag ggc gca ctg gaa gcg atg ggg tta aat ctc gaa gag ctg        336
Asp Val Gln Gly Ala Leu Glu Ala Met Gly Leu Asn Leu Glu Glu Leu
            100                 105                 110 att gat gaa gaa aat gac cca ggc ctc ggt aac ggt ggc ctg gga cgt        384
Ile Asp Glu Glu Asn Asp Pro Gly Leu Gly Asn Gly Gly Leu Gly Arg
            115                 120                 125 ctg gcg gct tgc ttc ctt gat tct ctg gcg acg tta ggg ttg ccg ggg        432
Leu Ala Ala Cys Phe Leu Asp Ser Leu Ala Thr Leu Gly Leu Pro Gly
        130                 135                 140 cgc ggt tac ggc atc cgc tat gac tac ggt atg ttc aag cag aac atc        480
Arg Gly Tyr Gly Ile Arg Tyr Asp Tyr Gly Met Phe Lys Gln Asn Ile
145                 150                 155                 160 gtt aac ggt agc cag aaa gag tcg cca gac tac tgg ctg gaa tac ggt        528
Val Asn Gly Ser Gln Lys Glu Ser Pro Asp Tyr Trp Leu Glu Tyr Gly
                165                 170                 175 aac ccg tgg gaa ttc aaa cgc cac aac acg cgc tat aaa gtc cgt ttt        576
Asn Pro Trp Glu Phe Lys Arg His Asn Thr Arg Tyr Lys Val Arg Phe
            180                 185                 190 ggc ggt cgc att cag cag gaa ggt aaa aaa acg cgc tgg att gaa acc        624
Gly Gly Arg Ile Gln Gln Glu Gly Lys Lys Thr Arg Trp Ile Glu Thr
            195                 200                 205 gaa gag att ctg gga gtc gct tac gat cag ata atc cct ggt tac gac        672
Glu Glu Ile Leu Gly Val Ala Tyr Asp Gln Ile Ile Pro Gly Tyr Asp
210                 215                 220 acc gac gcg acc aac acg ctg cgt ttg tgg agt gcg caa gcc agt agc        720
Thr Asp Ala Thr Asn Thr Leu Arg Leu Trp Ser Ala Gln Ala Ser Ser
225                 230                 235                 240 gaa att aac ctc ggt aaa ttc aac cag ggt gac tac ttc gcg gca gtg        768
Glu Ile Asn Leu Gly Lys Phe Asn Gln Gly Asp Tyr Phe Ala Ala Val
                245                 250                 255 gaa gat aaa aac cac tcc gag aac gta tct cgc gta ctg tat ccg gat        816
Glu Asp Lys Asn His Ser Glu Asn Val Ser Arg Val Leu Tyr Pro Asp
            260                 265                 270 gac tcc acc tac tcc ggg cgt gag ctg cgc ctg cgt cag gaa tac ttc        864
Asp Ser Thr Tyr Ser Gly Arg Glu Leu Arg Leu Arg Gln Glu Tyr Phe
            275                 280                 285 ctg gtt tcc tcg acc att cag gac att tta agc cgc cat tat cag ttg        912
Leu Val Ser Ser Thr Ile Gln Asp Ile Leu Ser Arg His Tyr Gln Leu
        290                 295                 300 cat aaa acc tac gat aac ctg gcg gat aaa atc gcg att cat ctc aat        960
His Lys Thr Tyr Asp Asn Leu Ala Asp Lys Ile Ala Ile His Leu Asn
305                 310                 315                 320 gat acc cat ccg gta ctg tcg att cct gag atg atg cgt ctg ctg atc       1008
Asp Thr His Pro Val Leu Ser Ile Pro Glu Met Met Arg Leu Leu Ile
                325                 330                 335 gat gag cac caa ttt agc tgg gac gac gcg ttt gag gtg tgt tgt cag       1056
Asp Glu His Gln Phe Ser Trp Asp Asp Ala Phe Glu Val Cys Cys Gln
            340                 345                 350 gtc ttc tcc tac act aac cac acg ctg atg agc gag gcg ctg gaa acc       1104
Val Phe Ser Tyr Thr Asn His Thr Leu Met Ser Glu Ala Leu Glu Thr
            355                 360                 365 tgg ccg gtt gat atg ctg ggt aaa att ctg ccg cgt cac ctg cag atc       1152
Trp Pro Val Asp Met Leu Gly Lys Ile Leu Pro Arg His Leu Gln Ile
370                 375                 380
```

```
atc ttt gaa atc aac gac tat ttc ctg aaa acc ttg cag gaa cag tat    1200
Ile Phe Glu Ile Asn Asp Tyr Phe Leu Lys Thr Leu Gln Glu Gln Tyr
385                 390                 395                 400 ccg aac gat acc gat ctg ctg gga cgg gcg tcg atc att gat gaa tcc    1248
Pro Asn Asp Thr Asp Leu Leu Gly Arg Ala Ser Ile Ile Asp Glu Ser
                405                 410                 415 aac ggt cgt cgt gtg cgt atg gcc tgg ctg gcg gtt gtt gtg agc cac    1296
Asn Gly Arg Arg Val Arg Met Ala Trp Leu Ala Val Val Val Ser His
            420                 425                 430 aaa gtt aac ggt gta tcg gaa ctg cac tct aat ctg atg gtg caa tcg    1344
Lys Val Asn Gly Val Ser Glu Leu His Ser Asn Leu Met Val Gln Ser
        435                 440                 445 ttg ttt gcc gac ttt gcg aaa atc ttc ccg ggt cgt ttc acc aac gtc    1392
Leu Phe Ala Asp Phe Ala Lys Ile Phe Pro Gly Arg Phe Thr Asn Val
    450                 455                 460 acc aac ggt gtg acg ccg cgt cgc tgg ctg gcg gta gcg aac cca tcg    1440
Thr Asn Gly Val Thr Pro Arg Arg Trp Leu Ala Val Ala Asn Pro Ser
465                 470                 475                 480 ctt tca gcc gtg ctg gac gaa cac ctg ggc cgt aac tgg cgc acc gac    1488
Leu Ser Ala Val Leu Asp Glu His Leu Gly Arg Asn Trp Arg Thr Asp
                485                 490                 495 ctt agc ctg ctt aat gag ctg caa caa cac tgt gat ttc cca atg gtt    1536
Leu Ser Leu Leu Asn Glu Leu Gln Gln His Cys Asp Phe Pro Met Val
                500                 505                 510 aat cac gct gtg cat cag gcg aag ctg gag aac aaa aag cgt ctg gca    1584
Asn His Ala Val His Gln Ala Lys Leu Glu Asn Lys Lys Arg Leu Ala
            515                 520                 525 gag tat atc gcc cag cag ctg aat gtg gtg gtg aat cca aag gcg ttg    1632
Glu Tyr Ile Ala Gln Gln Leu Asn Val Val Val Asn Pro Lys Ala Leu
        530                 535                 540 ttc gat gta caa atc aaa cgt att cac gaa tac aaa cgt caa ttg atg    1680
Phe Asp Val Gln Ile Lys Arg Ile His Glu Tyr Lys Arg Gln Leu Met
545                 550                 555                 560 aat gtg ttg cat gtg att acc cgc tat aac cgc atc aag gcc gac ccg    1728
Asn Val Leu His Val Ile Thr Arg Tyr Asn Arg Ile Lys Ala Asp Pro
                565                 570                 575 gat gcg aag tgg gta ccg cgc gtg aat att ttt ggc ggt aag gcg gct    1776
Asp Ala Lys Trp Val Pro Arg Val Asn Ile Phe Gly Gly Lys Ala Ala
                580                 585                 590 tcg gcc tat tac atg gcg aag cac att att cat ttg atc aat gac gta    1824
Ser Ala Tyr Tyr Met Ala Lys His Ile Ile His Leu Ile Asn Asp Val
            595                 600                 605 gcg aaa gtg atc aac aac gat ccg cag att ggc gat aag ctg aaa gtc    1872
Ala Lys Val Ile Asn Asn Asp Pro Gln Ile Gly Asp Lys Leu Lys Val
        610                 615                 620 gtg ttc atc ccg aac tac agc gtt agc ctg gcg cag ttg atc att ccg    1920
Val Phe Ile Pro Asn Tyr Ser Val Ser Leu Ala Gln Leu Ile Ile Pro
625                 630                 635                 640 gcg gca gat ctg tct gaa cag att tcg ctg gca ggg acg gaa gct tcc    1968
Ala Ala Asp Leu Ser Glu Gln Ile Ser Leu Ala Gly Thr Glu Ala Ser
                645                 650                 655 ggc acc agt aac atg aag ttt gcg ctt aac ggt gcg ctg act atc ggt    2016
Gly Thr Ser Asn Met Lys Phe Ala Leu Asn Gly Ala Leu Thr Ile Gly
                660                 665                 670 acg ttg gac ggt gcg aat gtc gag atg ctg gat cat gtc ggt gct gac    2064
Thr Leu Asp Gly Ala Asn Val Glu Met Leu Asp His Val Gly Ala Asp
            675                 680                 685 aat atc ttt att ttt ggt aac aca gcg gaa gaa gtg gaa gaa ctg cgt    2112
Asn Ile Phe Ile Phe Gly Asn Thr Ala Glu Glu Val Glu Glu Leu Arg
        690                 695                 700
```

```
cgt cag ggc tac aaa ccg cgt gaa tac tac gag aaa gat gag gag ctg        2160
Arg Gln Gly Tyr Lys Pro Arg Glu Tyr Tyr Glu Lys Asp Glu Glu Leu
705                 710                 715                 720 cat cag gtg ctg acg caa atc ggc agc ggt gta ttc agt ccg gaa gat        2208
His Gln Val Leu Thr Gln Ile Gly Ser Gly Val Phe Ser Pro Glu Asp
            725                 730                 735 ccg ggt cgc tat cgc gat ctg gtt gat tcg ctg atc aac ttc ggc gat        2256
Pro Gly Arg Tyr Arg Asp Leu Val Asp Ser Leu Ile Asn Phe Gly Asp
        740                 745                 750 cac tac cag gta ctg gcg gat tat cgc agc tat gtc gat tgt cag gat        2304
His Tyr Gln Val Leu Ala Asp Tyr Arg Ser Tyr Val Asp Cys Gln Asp
    755                 760                 765 aaa gtc gat gaa ctc tac gag ctt cag gaa gag tgg acc gca aaa gcg        2352
Lys Val Asp Glu Leu Tyr Glu Leu Gln Glu Glu Trp Thr Ala Lys Ala
770                 775                 780 atg ctg aac att gcc aat atg ggc tac ttc tct tct gac cgt act atc        2400
Met Leu Asn Ile Ala Asn Met Gly Tyr Phe Ser Ser Asp Arg Thr Ile
785                 790                 795                 800 aaa gag tac gcc gat cat atc tgg cat atc gat ccg gtg aga ttg taa        2448
Lys Glu Tyr Ala Asp His Ile Trp His Ile Asp Pro Val Arg Leu
            805                 810                 815

<210> SEQ ID NO 14
<211> LENGTH: 815
<212> TYPE: PRT
<213> ORGANISM: Escherichia coli

<400> SEQUENCE: 14

Met Asn Ala Pro Phe Thr Tyr Ser Ser Pro Thr Leu Ser Val Glu Ala
1               5                   10                  15

Leu Lys His Ser Ile Ala Tyr Lys Leu Met Phe Thr Ile Gly Lys Asp
            20                  25                  30

Pro Val Val Ala Asn Lys His Glu Trp Leu Asn Ala Thr Leu Phe Ala
        35                  40                  45

Val Arg Asp Arg Leu Val Glu Arg Trp Leu Arg Ser Asn Arg Ala Gln
    50                  55                  60

Leu Ser Gln Glu Thr Arg Gln Val Tyr Tyr Leu Ser Met Glu Phe Leu
65                  70                  75                  80

Ile Gly Arg Thr Leu Ser Asn Ala Met Leu Ser Leu Gly Ile Tyr Glu
                85                  90                  95

Asp Val Gln Gly Ala Leu Glu Ala Met Gly Leu Asn Leu Glu Glu Leu
            100                 105                 110

Ile Asp Glu Glu Asn Asp Pro Gly Leu Gly Asn Gly Gly Leu Gly Arg
        115                 120                 125

Leu Ala Ala Cys Phe Leu Asp Ser Leu Ala Thr Leu Gly Leu Pro Gly
    130                 135                 140

Arg Gly Tyr Gly Ile Arg Tyr Asp Tyr Gly Met Phe Lys Gln Asn Ile
145                 150                 155                 160

Val Asn Gly Ser Gln Lys Glu Ser Pro Asp Tyr Trp Leu Glu Tyr Gly
                165                 170                 175

Asn Pro Trp Glu Phe Lys Arg His Asn Thr Arg Tyr Lys Val Arg Phe
            180                 185                 190

Gly Gly Arg Ile Gln Gln Glu Gly Lys Lys Thr Arg Trp Ile Glu Thr
        195                 200                 205

Glu Glu Ile Leu Gly Val Ala Tyr Asp Gln Ile Ile Pro Gly Tyr Asp
    210                 215                 220
```

-continued

```
Thr Asp Ala Thr Asn Thr Leu Arg Leu Trp Ser Ala Gln Ala Ser Ser
225                 230                 235                 240

Glu Ile Asn Leu Gly Lys Phe Asn Gln Gly Asp Tyr Phe Ala Ala Val
            245                 250                 255

Glu Asp Lys Asn His Ser Glu Asn Val Ser Arg Val Leu Tyr Pro Asp
        260                 265                 270

Asp Ser Thr Tyr Ser Gly Arg Glu Leu Arg Leu Arg Gln Glu Tyr Phe
    275                 280                 285

Leu Val Ser Ser Thr Ile Gln Asp Ile Leu Ser Arg His Tyr Gln Leu
    290                 295                 300

His Lys Thr Tyr Asp Asn Leu Ala Asp Lys Ile Ala Ile His Leu Asn
305                 310                 315                 320

Asp Thr His Pro Val Leu Ser Ile Pro Glu Met Met Arg Leu Leu Ile
                325                 330                 335

Asp Glu His Gln Phe Ser Trp Asp Asp Ala Phe Glu Val Cys Cys Gln
            340                 345                 350

Val Phe Ser Tyr Thr Asn His Thr Leu Met Ser Glu Ala Leu Glu Thr
        355                 360                 365

Trp Pro Val Asp Met Leu Gly Lys Ile Leu Pro Arg His Leu Gln Ile
    370                 375                 380

Ile Phe Glu Ile Asn Asp Tyr Phe Leu Lys Thr Leu Gln Glu Gln Tyr
385                 390                 395                 400

Pro Asn Asp Thr Asp Leu Leu Gly Arg Ala Ser Ile Ile Asp Glu Ser
                405                 410                 415

Asn Gly Arg Arg Val Arg Met Ala Trp Leu Ala Val Val Ser His
            420                 425                 430

Lys Val Asn Gly Val Ser Glu Leu His Ser Asn Leu Met Val Gln Ser
        435                 440                 445

Leu Phe Ala Asp Phe Ala Lys Ile Phe Pro Gly Arg Phe Thr Asn Val
    450                 455                 460

Thr Asn Gly Val Thr Pro Arg Arg Trp Leu Ala Val Ala Asn Pro Ser
465                 470                 475                 480

Leu Ser Ala Val Leu Asp Glu His Leu Gly Arg Asn Trp Arg Thr Asp
                485                 490                 495

Leu Ser Leu Leu Asn Glu Leu Gln Gln His Cys Asp Phe Pro Met Val
            500                 505                 510

Asn His Ala Val His Gln Ala Lys Leu Glu Asn Lys Lys Arg Leu Ala
        515                 520                 525

Glu Tyr Ile Ala Gln Gln Leu Asn Val Val Asn Pro Lys Ala Leu
    530                 535                 540

Phe Asp Val Gln Ile Lys Arg Ile His Glu Tyr Lys Arg Gln Leu Met
545                 550                 555                 560

Asn Val Leu His Val Ile Thr Arg Tyr Asn Arg Ile Lys Ala Asp Pro
                565                 570                 575

Asp Ala Lys Trp Val Pro Arg Val Asn Ile Phe Gly Gly Lys Ala Ala
            580                 585                 590

Ser Ala Tyr Tyr Met Ala Lys His Ile Ile His Leu Ile Asn Asp Val
        595                 600                 605

Ala Lys Val Ile Asn Asn Asp Pro Gln Ile Gly Asp Lys Leu Lys Val
    610                 615                 620

Val Phe Ile Pro Asn Tyr Ser Val Ser Leu Ala Gln Leu Ile Ile Pro
625                 630                 635                 640

Ala Ala Asp Leu Ser Glu Gln Ile Ser Leu Ala Gly Thr Glu Ala Ser
```

```
                     645                 650                 655
Gly Thr Ser Asn Met Lys Phe Ala Leu Asn Gly Ala Leu Thr Ile Gly
                660                 665                 670

Thr Leu Asp Gly Ala Asn Val Glu Met Leu Asp His Val Gly Ala Asp
            675                 680                 685

Asn Ile Phe Ile Phe Gly Asn Thr Ala Glu Glu Val Glu Glu Leu Arg
        690                 695                 700

Arg Gln Gly Tyr Lys Pro Arg Glu Tyr Glu Lys Asp Glu Glu Leu
705                 710                 715                 720

His Gln Val Leu Thr Gln Ile Gly Ser Gly Val Phe Ser Pro Glu Asp
                725                 730                 735

Pro Gly Arg Tyr Arg Asp Leu Val Asp Ser Leu Ile Asn Phe Gly Asp
            740                 745                 750

His Tyr Gln Val Leu Ala Asp Tyr Arg Ser Tyr Val Asp Cys Gln Asp
        755                 760                 765

Lys Val Asp Glu Leu Tyr Glu Leu Gln Glu Glu Trp Thr Ala Lys Ala
770                 775                 780

Met Leu Asn Ile Ala Asn Met Gly Tyr Phe Ser Ser Asp Arg Thr Ile
785                 790                 795                 800

Lys Glu Tyr Ala Asp His Ile Trp His Ile Asp Pro Val Arg Leu
                805                 810                 815

<210> SEQ ID NO 15
<211> LENGTH: 1974
<212> TYPE: DNA
<213> ORGANISM: Escherichia coli
<220> FEATURE:
<221> NAME/KEY: CDS
<222> LOCATION: (1)..(1974)

<400> SEQUENCE: 15 atg aca caa ctc gcc att ggc aaa ccc gct ccc ctc ggc gcg cat tac    48
Met Thr Gln Leu Ala Ile Gly Lys Pro Ala Pro Leu Gly Ala His Tyr
1               5                   10                  15 gac ggt cag ggc gtc aac ttc aca ctt ttc tcc gct cat gcc gag cgg    96
Asp Gly Gln Gly Val Asn Phe Thr Leu Phe Ser Ala His Ala Glu Arg
            20                  25                  30 gta gaa ctg tgt gtc ttt gac gcc aat ggc cag gaa cat cgc tat gac   144
Val Glu Leu Cys Val Phe Asp Ala Asn Gly Gln Glu His Arg Tyr Asp
        35                  40                  45 ttg cca ggg cac agt ggc gac att tgg cac ggt tat ctg ccg gat gcg   192
Leu Pro Gly His Ser Gly Asp Ile Trp His Gly Tyr Leu Pro Asp Ala
    50                  55                  60 cgc ccg ggt ttg cgt tat ggt tat cgc gtt cat ggc ccc tgg caa ccc   240
Arg Pro Gly Leu Arg Tyr Gly Tyr Arg Val His Gly Pro Trp Gln Pro
65                  70                  75                  80 gcc gag ggg cat cgc ttt aac ccg gcg aag ttg ttg att gat cct tgc   288
Ala Glu Gly His Arg Phe Asn Pro Ala Lys Leu Leu Ile Asp Pro Cys
                85                  90                  95 gcg cgg caa att gac ggg gag ttt aaa gat aac ccg ctg ctg cac gcc   336
Ala Arg Gln Ile Asp Gly Glu Phe Lys Asp Asn Pro Leu Leu His Ala
            100                 105                 110 ggt cat aat gaa cct gac tat cgc gac aac gcc gcc att gcg ccg aaa   384
Gly His Asn Glu Pro Asp Tyr Arg Asp Asn Ala Ala Ile Ala Pro Lys
        115                 120                 125 tgc gta gtg gtg gtt gat cac tat gac tgg gaa gat gat gcc ccg ccg   432
Cys Val Val Val Val Asp His Tyr Asp Trp Glu Asp Asp Ala Pro Pro
    130                 135                 140
```

```
cgc acg ccg tgg ggc agc acc atc att tat gaa gcc cat gtc aaa gga    480
Arg Thr Pro Trp Gly Ser Thr Ile Ile Tyr Glu Ala His Val Lys Gly
145                 150                 155                 160 tta acg tac ttg cac ccg gag atc ccg gtc gag atc cgt ggc act tat    528
Leu Thr Tyr Leu His Pro Glu Ile Pro Val Glu Ile Arg Gly Thr Tyr
                165                 170                 175 aaa gcc ctc ggg cat ccg gtg atg atc aac tat ttg aaa caa ttg ggc    576
Lys Ala Leu Gly His Pro Val Met Ile Asn Tyr Leu Lys Gln Leu Gly
        180                 185                 190 att acc gcg ctg gaa ctg ctg cca gtg gcg cag ttt gcc agt gaa cca    624
Ile Thr Ala Leu Glu Leu Leu Pro Val Ala Gln Phe Ala Ser Glu Pro
    195                 200                 205 cgt ctg caa cgc atg ggg cta agt aac tac tgg ggt tac aac ccg gtg    672
Arg Leu Gln Arg Met Gly Leu Ser Asn Tyr Trp Gly Tyr Asn Pro Val
210                 215                 220 gcg atg ttt gcg ctg cat ccg gcg tat gcc tgc tcg cca gaa acg gcg    720
Ala Met Phe Ala Leu His Pro Ala Tyr Ala Cys Ser Pro Glu Thr Ala
225                 230                 235                 240 ctg gat gag ttt cgc gat gca atc aaa gca ctg cat aaa gcg ggt atc    768
Leu Asp Glu Phe Arg Asp Ala Ile Lys Ala Leu His Lys Ala Gly Ile
                245                 250                 255 gaa gtc att ctt gat atc gtg ctc aac cat agt gcg gaa ctg gac ctc    816
Glu Val Ile Leu Asp Ile Val Leu Asn His Ser Ala Glu Leu Asp Leu
            260                 265                 270 gac ggc ccg tta ttc tcg ctg cgt ggg atc gat aac cgt agc tat tat    864
Asp Gly Pro Leu Phe Ser Leu Arg Gly Ile Asp Asn Arg Ser Tyr Tyr
        275                 280                 285 tgg ata aga gaa gac ggc gat tat cac aac tgg acc ggt tgc ggc aac    912
Trp Ile Arg Glu Asp Gly Asp Tyr His Asn Trp Thr Gly Cys Gly Asn
    290                 295                 300 acg ctc aat ttg agt cat ccg gcg gtg gtg gat tat gcc agc gcc tgc    960
Thr Leu Asn Leu Ser His Pro Ala Val Val Asp Tyr Ala Ser Ala Cys
305                 310                 315                 320 ctg cgt tat tgg gta gaa acc tgc cac gtc gat ggt ttc cgc ttt gat   1008
Leu Arg Tyr Trp Val Glu Thr Cys His Val Asp Gly Phe Arg Phe Asp
                325                 330                 335 ctg gcg gca gtc atg ggc cgt acg cca gag ttc cgt cag gat gcg ccg   1056
Leu Ala Ala Val Met Gly Arg Thr Pro Glu Phe Arg Gln Asp Ala Pro
            340                 345                 350 ttg ttt acc gct atc cag aac tgc ccg gtg ctc tcg cag gtg aag tta   1104
Leu Phe Thr Ala Ile Gln Asn Cys Pro Val Leu Ser Gln Val Lys Leu
        355                 360                 365 att gct gaa ccg tgg gat atc gct cct ggt ggt tat cag gtg gga aat   1152
Ile Ala Glu Pro Trp Asp Ile Ala Pro Gly Gly Tyr Gln Val Gly Asn
370                 375                 380 ttc ccg ccg ctg ttt gcc gag tgg aac gat cat ttc cgc gat gct gcc   1200
Phe Pro Pro Leu Phe Ala Glu Trp Asn Asp His Phe Arg Asp Ala Ala
385                 390                 395                 400 cgt cgt ttc tgg cta cat tat gat ttg cct ctg ggg gcg ttt gcc ggg   1248
Arg Arg Phe Trp Leu His Tyr Asp Leu Pro Leu Gly Ala Phe Ala Gly
                405                 410                 415 cgt ttt gct gcc tcc agc gat gtt ttt aaa cgt aat ggt cgt ctg ccg   1296
Arg Phe Ala Ala Ser Ser Asp Val Phe Lys Arg Asn Gly Arg Leu Pro
            420                 425                 430 agt gcc gcg att aat ctc gtc acc gcg cat gac ggt ttt acg ctt cgc   1344
Ser Ala Ala Ile Asn Leu Val Thr Ala His Asp Gly Phe Thr Leu Arg
        435                 440                 445 gac tgc gtt tgc ttc aac cat aaa cac aat gaa gca aac gga gaa gaa   1392
Asp Cys Val Cys Phe Asn His Lys His Asn Glu Ala Asn Gly Glu Glu
450                 455                 460
```

-continued

```
aat cgc gac ggg acc aac aac aat tac agt aac aat cat ggt aaa gaa      1440
Asn Arg Asp Gly Thr Asn Asn Asn Tyr Ser Asn Asn His Gly Lys Glu
465                 470                 475                 480 ggg tta ggc ggt tct ctt gac ctg gtt gaa cgg cgg cgc gac agc att      1488
Gly Leu Gly Gly Ser Leu Asp Leu Val Glu Arg Arg Arg Asp Ser Ile
                485                 490                 495 cac gcc ctg tta aca acg ttg ttg ctc tcc cag ggt acg ccg atg tta      1536
His Ala Leu Leu Thr Thr Leu Leu Leu Ser Gln Gly Thr Pro Met Leu
        500                 505                 510 ctg gcc ggt gac gaa cat ggt cac agc cag cat ggc aat aac aat gcc      1584
Leu Ala Gly Asp Glu His Gly His Ser Gln His Gly Asn Asn Asn Ala
    515                 520                 525 tac tgt cag gat aac caa tta acc tgg ttg gac tgg tcg cag gca agc      1632
Tyr Cys Gln Asp Asn Gln Leu Thr Trp Leu Asp Trp Ser Gln Ala Ser
530                 535                 540 agt ggt tta acc gca ttt acc gcc gcg tta atc cat ctg cgc aag cgc      1680
Ser Gly Leu Thr Ala Phe Thr Ala Ala Leu Ile His Leu Arg Lys Arg
545                 550                 555                 560 att ccc gct ttg gtg gag aat cgc tgg tgg gaa gaa ggc gac ggc aat      1728
Ile Pro Ala Leu Val Glu Asn Arg Trp Trp Glu Glu Gly Asp Gly Asn
                565                 570                 575 gtc cgt tgg cta aat cga tat gct caa cct tta agc acg gat gag tgg      1776
Val Arg Trp Leu Asn Arg Tyr Ala Gln Pro Leu Ser Thr Asp Glu Trp
        580                 585                 590 caa aac ggg ccg aaa cag ctg caa att ctg ctc tcg gat cgc ttt ttg      1824
Gln Asn Gly Pro Lys Gln Leu Gln Ile Leu Leu Ser Asp Arg Phe Leu
    595                 600                 605 atc gca att aac gcc acg ctt gag gta aca gag att gtt tta cct gct      1872
Ile Ala Ile Asn Ala Thr Leu Glu Val Thr Glu Ile Val Leu Pro Ala
610                 615                 620 ggg gag tgg cac gcc att ccc cca ttc gct gga gag gat aac cca gtg      1920
Gly Glu Trp His Ala Ile Pro Pro Phe Ala Gly Glu Asp Asn Pro Val
625                 630                 635                 640 att acg gct gtc tgg cag gga cct gca cac gga ttg tgt gtg ttc cag      1968
Ile Thr Ala Val Trp Gln Gly Pro Ala His Gly Leu Cys Val Phe Gln
                645                 650                 655 aga tga                                                              1974
Arg
```

<210> SEQ ID NO 16
<211> LENGTH: 657
<212> TYPE: PRT
<213> ORGANISM: Escherichia coli

<400> SEQUENCE: 16

```
Met Thr Gln Leu Ala Ile Gly Lys Pro Ala Pro Leu Gly Ala His Tyr
1               5                   10                  15

Asp Gly Gln Gly Val Asn Phe Thr Leu Phe Ser Ala His Ala Glu Arg
                20                  25                  30

Val Glu Leu Cys Val Phe Asp Ala Asn Gly Gln Glu His Arg Tyr Asp
            35                  40                  45

Leu Pro Gly His Ser Gly Asp Ile Trp His Gly Tyr Leu Pro Asp Ala
        50                  55                  60

Arg Pro Gly Leu Arg Tyr Gly Tyr Arg Val His Gly Pro Trp Gln Pro
65                  70                  75                  80

Ala Glu Gly His Arg Phe Asn Pro Ala Lys Leu Leu Ile Asp Pro Cys
                85                  90                  95

Ala Arg Gln Ile Asp Gly Glu Phe Lys Asp Asn Pro Leu Leu His Ala
```

```
                100             105             110
Gly His Asn Glu Pro Asp Tyr Arg Asp Asn Ala Ala Ile Ala Pro Lys
            115                 120                 125
Cys Val Val Val Asp His Tyr Asp Trp Glu Asp Ala Pro Pro
130                 135                 140
Arg Thr Pro Trp Gly Ser Thr Ile Ile Tyr Glu Ala His Val Lys Gly
145                 150                 155                 160
Leu Thr Tyr Leu His Pro Glu Ile Pro Val Glu Ile Arg Gly Thr Tyr
                165                 170                 175
Lys Ala Leu Gly His Pro Val Met Ile Asn Tyr Leu Lys Gln Leu Gly
            180                 185                 190
Ile Thr Ala Leu Glu Leu Leu Pro Val Ala Gln Phe Ala Ser Glu Pro
            195                 200                 205
Arg Leu Gln Arg Met Gly Leu Ser Asn Tyr Trp Gly Tyr Asn Pro Val
210                 215                 220
Ala Met Phe Ala Leu His Pro Ala Tyr Ala Cys Ser Pro Glu Thr Ala
225                 230                 235                 240
Leu Asp Glu Phe Arg Asp Ala Ile Lys Ala Leu His Lys Ala Gly Ile
                245                 250                 255
Glu Val Ile Leu Asp Ile Val Leu Asn His Ser Ala Glu Leu Asp Leu
            260                 265                 270
Asp Gly Pro Leu Phe Ser Leu Arg Gly Ile Asp Asn Arg Ser Tyr Tyr
            275                 280                 285
Trp Ile Arg Glu Asp Gly Asp Tyr His Asn Trp Thr Gly Cys Gly Asn
290                 295                 300
Thr Leu Asn Leu Ser His Pro Ala Val Val Asp Tyr Ala Ser Ala Cys
305                 310                 315                 320
Leu Arg Tyr Trp Val Glu Thr Cys His Val Asp Gly Phe Arg Phe Asp
                325                 330                 335
Leu Ala Ala Val Met Gly Arg Thr Pro Glu Phe Arg Gln Asp Ala Pro
            340                 345                 350
Leu Phe Thr Ala Ile Gln Asn Cys Pro Val Leu Ser Gln Val Lys Leu
            355                 360                 365
Ile Ala Glu Pro Trp Asp Ile Ala Pro Gly Gly Tyr Gln Val Gly Asn
            370                 375                 380
Phe Pro Pro Leu Phe Ala Glu Trp Asn Asp His Phe Arg Asp Ala Ala
385                 390                 395                 400
Arg Arg Phe Trp Leu His Tyr Asp Leu Pro Leu Gly Ala Phe Ala Gly
                405                 410                 415
Arg Phe Ala Ala Ser Ser Asp Val Phe Lys Arg Asn Gly Arg Leu Pro
            420                 425                 430
Ser Ala Ala Ile Asn Leu Val Thr Ala His Asp Gly Phe Thr Leu Arg
            435                 440                 445
Asp Cys Val Cys Phe Asn His Lys His Asn Glu Ala Asn Gly Glu Glu
            450                 455                 460
Asn Arg Asp Gly Thr Asn Asn Tyr Ser Asn Asn His Gly Lys Glu
465                 470                 475                 480
Gly Leu Gly Gly Ser Leu Asp Leu Val Glu Arg Arg Arg Asp Ser Ile
                485                 490                 495
His Ala Leu Leu Thr Thr Leu Leu Leu Ser Gln Gly Thr Pro Met Leu
            500                 505                 510
Leu Ala Gly Asp Glu His Gly His Ser Gln His Gly Asn Asn Asn Ala
            515                 520                 525
```

```
Tyr Cys Gln Asp Asn Gln Leu Thr Trp Leu Asp Trp Ser Gln Ala Ser
        530                 535                 540

Ser Gly Leu Thr Ala Phe Thr Ala Ala Leu Ile His Leu Arg Lys Arg
545                 550                 555                 560

Ile Pro Ala Leu Val Glu Asn Arg Trp Trp Glu Glu Gly Asp Gly Asn
                565                 570                 575

Val Arg Trp Leu Asn Arg Tyr Ala Gln Pro Leu Ser Thr Asp Glu Trp
            580                 585                 590

Gln Asn Gly Pro Lys Gln Leu Gln Ile Leu Leu Ser Asp Arg Phe Leu
        595                 600                 605

Ile Ala Ile Asn Ala Thr Leu Glu Val Thr Glu Ile Val Leu Pro Ala
    610                 615                 620

Gly Glu Trp His Ala Ile Pro Pro Phe Ala Gly Glu Asp Asn Pro Val
625                 630                 635                 640

Ile Thr Ala Val Trp Gln Gly Pro Ala His Gly Leu Cys Val Phe Gln
                645                 650                 655

Arg

<210> SEQ ID NO 17
<211> LENGTH: 2187
<212> TYPE: DNA
<213> ORGANISM: Escherichia coli
<220> FEATURE:
<221> NAME/KEY: CDS
<222> LOCATION: (1)..(2187)

<400> SEQUENCE: 17 atg tcc gat cgt atc gat aga gac gtg att aac gcg cta att gca ggc      48
Met Ser Asp Arg Ile Asp Arg Asp Val Ile Asn Ala Leu Ile Ala Gly
1               5                   10                  15 cat ttt gcg gat cct ttt tcc gta ctg gga atg cat aaa acc acc gcg      96
His Phe Ala Asp Pro Phe Ser Val Leu Gly Met His Lys Thr Thr Ala
                20                  25                  30 gga ctg gaa gtc cgt gcc ctt tta ccc gac gct acc gat gtg tgg gtg     144
Gly Leu Glu Val Arg Ala Leu Leu Pro Asp Ala Thr Asp Val Trp Val
            35                  40                  45 att gaa ccg aaa acc ggg cgc aaa ctc gca aaa ctg gag tgt ctc gac     192
Ile Glu Pro Lys Thr Gly Arg Lys Leu Ala Lys Leu Glu Cys Leu Asp
        50                  55                  60 tca cgg gga ttc ttt agc ggc gtc att ccg cga cgt aag aat ttt ttc     240
Ser Arg Gly Phe Phe Ser Gly Val Ile Pro Arg Arg Lys Asn Phe Phe
65                  70                  75                  80 cgc tat cag ttg gct gtt gtc tgg cat ggt cag caa aac ctg att gat     288
Arg Tyr Gln Leu Ala Val Val Trp His Gly Gln Gln Asn Leu Ile Asp
                85                  90                  95 gat cct tac cgt ttt ggt ccg cta atc cag gaa atg gat gcc tgg cta     336
Asp Pro Tyr Arg Phe Gly Pro Leu Ile Gln Glu Met Asp Ala Trp Leu
                100                 105                 110 tta tct gaa ggt act cac ctg cgc ccg tat gaa acc tta ggc gcg cat     384
Leu Ser Glu Gly Thr His Leu Arg Pro Tyr Glu Thr Leu Gly Ala His
            115                 120                 125 gca gat act atg gat ggc gtc aca ggt acg cgt ttc tct gtc tgg gct     432
Ala Asp Thr Met Asp Gly Val Thr Gly Thr Arg Phe Ser Val Trp Ala
        130                 135                 140 cca aac gcc cgt cgg gtc tcg gtg gtt ggg caa ttc aac tac tgg gac     480
Pro Asn Ala Arg Arg Val Ser Val Val Gly Gln Phe Asn Tyr Trp Asp
145                 150                 155                 160 ggt cgc cgt cac ccg atg cgc ctg cgt aaa gag agc ggc atc tgg gaa     528
```

```
Gly Arg Arg His Pro Met Arg Leu Arg Lys Glu Ser Gly Ile Trp Glu
            165                 170                 175 ctg ttt atc cct ggg gcg cat aac ggt cag ctc tat aaa tac gag atg      576
Leu Phe Ile Pro Gly Ala His Asn Gly Gln Leu Tyr Lys Tyr Glu Met
        180                 185                 190 att gat gcc aat ggc aac ttg cgt ctg aag tcc gac cct tat gcc ttt      624
Ile Asp Ala Asn Gly Asn Leu Arg Leu Lys Ser Asp Pro Tyr Ala Phe
            195                 200                 205 gaa gcg caa atg cgc ccg gaa acc gcg tct ctt att tgc ggg ctg ccg      672
Glu Ala Gln Met Arg Pro Glu Thr Ala Ser Leu Ile Cys Gly Leu Pro
    210                 215                 220 gaa aag gtt gta cag act gaa gag cgc aaa aaa gcg aat cag ttt gat      720
Glu Lys Val Val Gln Thr Glu Glu Arg Lys Lys Ala Asn Gln Phe Asp
225                 230                 235                 240 gcg cca atc tct att tat gaa gtt cac ctg ggt tcc tgg cgt cgc cac      768
Ala Pro Ile Ser Ile Tyr Glu Val His Leu Gly Ser Trp Arg Arg His
                245                 250                 255 acc gac aac aat ttc tgg ttg agc tac cgc gag ctg gcc gat caa ctg      816
Thr Asp Asn Asn Phe Trp Leu Ser Tyr Arg Glu Leu Ala Asp Gln Leu
            260                 265                 270 gtg cct tat gct aaa tgg atg ggc ttt acc cac ctc gaa cta ctg ccc      864
Val Pro Tyr Ala Lys Trp Met Gly Phe Thr His Leu Glu Leu Leu Pro
        275                 280                 285 att aac gag cat ccc ttc gat ggc agt tgg ggt tat cag cca acc ggc      912
Ile Asn Glu His Pro Phe Asp Gly Ser Trp Gly Tyr Gln Pro Thr Gly
    290                 295                 300 ctg tat gcg cca acc cgc cgt ttt ggt act cgc gac gac ttc cgt tat      960
Leu Tyr Ala Pro Thr Arg Arg Phe Gly Thr Arg Asp Asp Phe Arg Tyr
305                 310                 315                 320 ttc att gat gcc gca cac gca gct ggt ctg aac gtg att ctc gac tgg     1008
Phe Ile Asp Ala Ala His Ala Ala Gly Leu Asn Val Ile Leu Asp Trp
                325                 330                 335 gtg cca ggc cac ttc ccg act gat gac ttt gcg ctt gcc gaa ttt gat     1056
Val Pro Gly His Phe Pro Thr Asp Asp Phe Ala Leu Ala Glu Phe Asp
            340                 345                 350 ggc acg aac ttg tat gaa cac agc gat ccg cgt gaa ggc tat cat cag     1104
Gly Thr Asn Leu Tyr Glu His Ser Asp Pro Arg Glu Gly Tyr His Gln
        355                 360                 365 gac tgg aac acg ctg atc tac aac tat ggt cgc cgt gaa gtc agt aac     1152
Asp Trp Asn Thr Leu Ile Tyr Asn Tyr Gly Arg Arg Glu Val Ser Asn
    370                 375                 380 ttc ctc gtc ggt aac gcg ctt tac tgg att gaa cgt ttt ggt att gat     1200
Phe Leu Val Gly Asn Ala Leu Tyr Trp Ile Glu Arg Phe Gly Ile Asp
385                 390                 395                 400 gcg ctg cgc gtc gat gcg gtg gcg tca atg att tat cgc gac tac agc     1248
Ala Leu Arg Val Asp Ala Val Ala Ser Met Ile Tyr Arg Asp Tyr Ser
                405                 410                 415 cgt aaa gag ggg gag tgg atc ccg aac gaa ttt ggc ggg cgc gag aat     1296
Arg Lys Glu Gly Glu Trp Ile Pro Asn Glu Phe Gly Gly Arg Glu Asn
            420                 425                 430 ctt gaa gcg att gaa ttc ttg cgt aat acc aac cgt att ctt ggt gag     1344
Leu Glu Ala Ile Glu Phe Leu Arg Asn Thr Asn Arg Ile Leu Gly Glu
        435                 440                 445 cag gtt tcc ggt gcg gtg aca atg gct gag gag tct acc gat ttc cct     1392
Gln Val Ser Gly Ala Val Thr Met Ala Glu Glu Ser Thr Asp Phe Pro
    450                 455                 460 ggc gtt tct cgt ccg cag gat atg ggc ggt ctg ggc ttc tgg tac aag     1440
Gly Val Ser Arg Pro Gln Asp Met Gly Gly Leu Gly Phe Trp Tyr Lys
465                 470                 475                 480
```

```
tgg aac ctc ggc tgg atg cat gac acc ctg gac tac atg aag ctc gac      1488
Trp Asn Leu Gly Trp Met His Asp Thr Leu Asp Tyr Met Lys Leu Asp
                485                 490                 495 ccg gtt tat cgt cag tat cat cac gat aaa ctg acc ttc ggg att ctc      1536
Pro Val Tyr Arg Gln Tyr His His Asp Lys Leu Thr Phe Gly Ile Leu
            500                 505                 510 tac aac tac act gaa aac ttc gtc ctg ccg ttg tcg cat gat gaa gtg      1584
Tyr Asn Tyr Thr Glu Asn Phe Val Leu Pro Leu Ser His Asp Glu Val
        515                 520                 525 gtc cac ggt aaa aaa tcg att ctc gac cgc atg ccg ggc gac gca tgg      1632
Val His Gly Lys Lys Ser Ile Leu Asp Arg Met Pro Gly Asp Ala Trp
    530                 535                 540 cag aaa ttc gcg aac ctg cgc gcc tat tat ggc tgg atg tgg gca ttc      1680
Gln Lys Phe Ala Asn Leu Arg Ala Tyr Tyr Gly Trp Met Trp Ala Phe
545                 550                 555                 560 ccg ggc aag aaa cta ctg ttc atg ggt aac gaa ttt gcc cag ggc cgc      1728
Pro Gly Lys Lys Leu Leu Phe Met Gly Asn Glu Phe Ala Gln Gly Arg
                565                 570                 575 gag tgg aac cat gac gcc agc ctc gac tgg cat ctg ttg gaa ggc ggc      1776
Glu Trp Asn His Asp Ala Ser Leu Asp Trp His Leu Leu Glu Gly Gly
            580                 585                 590 gat aac tgg cac cac ggt gtc cag cgt ctg gtg cgc gat ctg aac ctc      1824
Asp Asn Trp His His Gly Val Gln Arg Leu Val Arg Asp Leu Asn Leu
        595                 600                 605 acc tac cgc cac cat aaa gca atg cat gaa ctg gat ttt gac ccg tac      1872
Thr Tyr Arg His His Lys Ala Met His Glu Leu Asp Phe Asp Pro Tyr
    610                 615                 620 ggc ttt gaa tgg ctg gtg gtg gat gac aaa gaa cgc tcg gtg ctg atc      1920
Gly Phe Glu Trp Leu Val Val Asp Asp Lys Glu Arg Ser Val Leu Ile
625                 630                 635                 640 ttt gtg cgt cgc gat aaa gag ggt aac gaa atc atc gtt gcc agt aac      1968
Phe Val Arg Arg Asp Lys Glu Gly Asn Glu Ile Ile Val Ala Ser Asn
                645                 650                 655 ttt acg ccg gta ccg cgt cat gat tat cgc ttc ggc ata aac cag ccg      2016
Phe Thr Pro Val Pro Arg His Asp Tyr Arg Phe Gly Ile Asn Gln Pro
            660                 665                 670 ggc aaa tgg cgt gaa atc ctc aat acc gat tcc atg cac tat cac ggc      2064
Gly Lys Trp Arg Glu Ile Leu Asn Thr Asp Ser Met His Tyr His Gly
        675                 680                 685 agt aat gca ggc aat ggc ggc acg gta cac agc gat gag att gcc agc      2112
Ser Asn Ala Gly Asn Gly Gly Thr Val His Ser Asp Glu Ile Ala Ser
    690                 695                 700 cac ggt cgt cag cat tca cta agc ctg acg cta cca ccg ctg gcc act      2160
His Gly Arg Gln His Ser Leu Ser Leu Thr Leu Pro Pro Leu Ala Thr
705                 710                 715                 720 atc tgg ctg gtt cgg gag gca gaa tga                                   2187
Ile Trp Leu Val Arg Glu Ala Glu
                725
```

<210> SEQ ID NO 18
<211> LENGTH: 728
<212> TYPE: PRT
<213> ORGANISM: Escherichia coli

<400> SEQUENCE: 18

```
Met Ser Asp Arg Ile Asp Arg Asp Val Ile Asn Ala Leu Ile Ala Gly
1               5                   10                  15

His Phe Ala Asp Pro Phe Ser Val Leu Gly Met His Lys Thr Thr Ala
                20                  25                  30

Gly Leu Glu Val Arg Ala Leu Leu Pro Asp Ala Thr Asp Val Trp Val
```

-continued

```
                35                  40                  45
Ile Glu Pro Lys Thr Gly Arg Lys Leu Ala Lys Leu Glu Cys Leu Asp
         50                  55                  60
Ser Arg Gly Phe Phe Ser Gly Val Ile Pro Arg Lys Asn Phe Phe
 65                  70                  75                  80
Arg Tyr Gln Leu Ala Val Val Trp His Gly Gln Gln Asn Leu Ile Asp
                 85                  90                  95
Asp Pro Tyr Arg Phe Gly Pro Leu Ile Gln Glu Met Asp Ala Trp Leu
                100                 105                 110
Leu Ser Glu Gly Thr His Leu Arg Pro Tyr Glu Thr Leu Gly Ala His
                115                 120                 125
Ala Asp Thr Met Asp Gly Val Thr Gly Thr Arg Phe Ser Val Trp Ala
            130                 135                 140
Pro Asn Ala Arg Arg Val Ser Val Val Gly Gln Phe Asn Tyr Trp Asp
145                 150                 155                 160
Gly Arg Arg His Pro Met Arg Leu Arg Lys Glu Ser Gly Ile Trp Glu
                165                 170                 175
Leu Phe Ile Pro Gly Ala His Asn Gly Gln Leu Tyr Lys Tyr Glu Met
            180                 185                 190
Ile Asp Ala Asn Gly Asn Leu Arg Leu Lys Ser Asp Pro Tyr Ala Phe
            195                 200                 205
Glu Ala Gln Met Arg Pro Glu Thr Ala Ser Leu Ile Cys Gly Leu Pro
            210                 215                 220
Glu Lys Val Val Gln Thr Glu Arg Lys Lys Ala Asn Gln Phe Asp
225                 230                 235                 240
Ala Pro Ile Ser Ile Tyr Glu Val His Leu Gly Ser Trp Arg Arg His
                245                 250                 255
Thr Asp Asn Asn Phe Trp Leu Ser Tyr Arg Glu Leu Ala Asp Gln Leu
            260                 265                 270
Val Pro Tyr Ala Lys Trp Met Gly Phe Thr His Leu Glu Leu Leu Pro
            275                 280                 285
Ile Asn Glu His Pro Phe Asp Gly Ser Trp Gly Tyr Gln Pro Thr Gly
            290                 295                 300
Leu Tyr Ala Pro Thr Arg Arg Phe Gly Thr Arg Asp Asp Phe Arg Tyr
305                 310                 315                 320
Phe Ile Asp Ala Ala His Ala Ala Gly Leu Asn Val Ile Leu Asp Trp
                325                 330                 335
Val Pro Gly His Phe Pro Thr Asp Asp Phe Ala Leu Ala Glu Phe Asp
            340                 345                 350
Gly Thr Asn Leu Tyr Glu His Ser Asp Pro Arg Glu Gly Tyr His Gln
            355                 360                 365
Asp Trp Asn Thr Leu Ile Tyr Asn Tyr Gly Arg Arg Glu Val Ser Asn
        370                 375                 380
Phe Leu Val Gly Asn Ala Leu Tyr Trp Ile Glu Arg Phe Gly Ile Asp
385                 390                 395                 400
Ala Leu Arg Val Asp Ala Val Ala Ser Met Ile Tyr Arg Asp Tyr Ser
                405                 410                 415
Arg Lys Glu Gly Glu Trp Ile Pro Asn Glu Phe Gly Gly Arg Glu Asn
            420                 425                 430
Leu Glu Ala Ile Glu Phe Leu Arg Asn Thr Asn Arg Ile Leu Gly Glu
            435                 440                 445
Gln Val Ser Gly Ala Val Thr Met Ala Glu Glu Ser Thr Asp Phe Pro
        450                 455                 460
```

```
Gly Val Ser Arg Pro Gln Asp Met Gly Gly Leu Gly Phe Trp Tyr Lys
465                 470                 475                 480

Trp Asn Leu Gly Trp Met His Asp Thr Leu Asp Tyr Met Lys Leu Asp
                485                 490                 495

Pro Val Tyr Arg Gln Tyr His Asp Lys Leu Thr Phe Gly Ile Leu
            500                 505                 510

Tyr Asn Tyr Thr Glu Asn Phe Val Leu Pro Leu Ser His Asp Glu Val
                515                 520                 525

Val His Gly Lys Lys Ser Ile Leu Asp Arg Met Pro Gly Asp Ala Trp
    530                 535                 540

Gln Lys Phe Ala Asn Leu Arg Ala Tyr Tyr Gly Trp Met Trp Ala Phe
545                 550                 555                 560

Pro Gly Lys Lys Leu Leu Phe Met Gly Asn Glu Phe Ala Gln Gly Arg
                565                 570                 575

Glu Trp Asn His Asp Ala Ser Leu Asp Trp His Leu Leu Glu Gly Gly
                580                 585                 590

Asp Asn Trp His His Gly Val Gln Arg Leu Val Arg Asp Leu Asn Leu
                595                 600                 605

Thr Tyr Arg His His Lys Ala Met His Glu Leu Asp Phe Asp Pro Tyr
        610                 615                 620

Gly Phe Glu Trp Leu Val Val Asp Asp Lys Glu Arg Ser Val Leu Ile
625                 630                 635                 640

Phe Val Arg Arg Asp Lys Glu Gly Asn Glu Ile Ile Val Ala Ser Asn
                645                 650                 655

Phe Thr Pro Val Pro Arg His Asp Tyr Arg Phe Gly Ile Asn Gln Pro
                660                 665                 670

Gly Lys Trp Arg Glu Ile Leu Asn Thr Asp Ser Met His Tyr His Gly
            675                 680                 685

Ser Asn Ala Gly Asn Gly Gly Thr Val His Ser Asp Glu Ile Ala Ser
            690                 695                 700

His Gly Arg Gln His Ser Leu Ser Leu Thr Leu Pro Pro Leu Ala Thr
705                 710                 715                 720

Ile Trp Leu Val Arg Glu Ala Glu
                725

<210> SEQ ID NO 19
<211> LENGTH: 201
<212> TYPE: DNA
<213> ORGANISM: Escherichia coli
<220> FEATURE:
<221> NAME/KEY: CDS
<222> LOCATION: (1)..(201)

<400> SEQUENCE: 19 atg gat cat agt ctt aat tct tta aat aat ttc gat ttc ctg gcg cgt      48
Met Asp His Ser Leu Asn Ser Leu Asn Asn Phe Asp Phe Leu Ala Arg
1               5                   10                  15 agt ttt gcc aga atg cac gca gaa ggt cgc ccg gtc gat att ctg gcc      96
Ser Phe Ala Arg Met His Ala Glu Gly Arg Pro Val Asp Ile Leu Ala
                20                  25                  30 gtt act ggt aac atg gat gaa gaa cat aga acc tgg ttt tgc gca cgt     144
Val Thr Gly Asn Met Asp Glu Glu His Arg Thr Trp Phe Cys Ala Arg
        35                  40                  45 tat gcc tgg tat tgt caa cag atg atg cag gca aga gag ctg gag tta     192
Tyr Ala Trp Tyr Cys Gln Gln Met Met Gln Ala Arg Glu Leu Glu Leu
    50                  55                  60
```

```
gag cac tga                                                         201
Glu His
65

<210> SEQ ID NO 20
<211> LENGTH: 66
<212> TYPE: PRT
<213> ORGANISM: Escherichia coli

<400> SEQUENCE: 20

Met Asp His Ser Leu Asn Ser Leu Asn Asn Phe Asp Phe Leu Ala Arg
1               5                   10                  15

Ser Phe Ala Arg Met His Ala Glu Gly Arg Pro Val Asp Ile Leu Ala
            20                  25                  30

Val Thr Gly Asn Met Asp Glu Glu His Arg Thr Trp Phe Cys Ala Arg
        35                  40                  45

Tyr Ala Trp Tyr Cys Gln Gln Met Met Gln Ala Arg Glu Leu Glu Leu
    50                  55                  60

Glu His
65
```